US012559714B2

(12) United States Patent
Duan et al.

(10) Patent No.: US 12,559,714 B2
(45) Date of Patent: Feb. 24, 2026

(54) *BIFIDOBACTERIUM ANIMALIS* SUBSP. *LACTIS* AND USE THEREOF

(71) Applicant: Wisbiom (Beijing) Biotechnology Co., Ltd., Beijing (CN)

(72) Inventors: Yunfeng Duan, Beijing (CN); Ye Zhang, Beijing (CN); Hua Liang, Beijing (CN); Zhi Liu, Beijing (CN)

(73) Assignee: WISBIOM (BEIJING) BIOTECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/276,657

(22) PCT Filed: Apr. 8, 2022

(86) PCT No.: PCT/CN2022/085752
§ 371 (c)(1),
(2) Date: Aug. 10, 2023

(87) PCT Pub. No.: WO2022/171203
PCT Pub. Date: Aug. 18, 2022

(65) Prior Publication Data
US 2024/0417674 A1 Dec. 19, 2024

(30) Foreign Application Priority Data

Feb. 10, 2021 (CN) ......................... 202110185142.X
Feb. 10, 2021 (CN) ......................... 202110185144.9

(51) Int. Cl.
*C12N 1/20* (2006.01)

(52) U.S. Cl.
CPC .................................... *C12N 1/20* (2013.01)

(58) Field of Classification Search
CPC ...................................................... C12N 1/20
See application file for complete search history.

(56) References Cited

U.S. PATENT DOCUMENTS

| | | | |
|---|---|---|---|
| 2017/0252382 A1 | 9/2017 | Leser et al. | |
| 2019/0070225 A1 | 3/2019 | Strandwitz et al. | |

FOREIGN PATENT DOCUMENTS

| | | |
|---|---|---|
| CA | 3205469 A1 | 6/2022 |
| CN | 104884610 A | 9/2015 |
| CN | 105603066 A | 5/2016 |
| CN | 109069554 A | 12/2018 |
| CN | 111172074 A | 5/2020 |
| CN | 111500506 A | 8/2020 |
| CN | 111588021 A | 8/2020 |
| CN | 112956696 A | 6/2021 |
| CN | 112980725 A | 6/2021 |
| JP | 2004531477 A | 10/2004 |
| JP | 2007507485 A | 3/2007 |
| JP | 2013507394 A | 3/2013 |
| JP | 2015530406 A | 10/2015 |
| JP | 2019513390 A | 5/2019 |
| JP | 2019523278 A | 8/2019 |
| JP | 2020523326 A | 8/2020 |
| KR | 101611832 B1 | 4/2016 |
| WO | 2002032441 A1 | 4/2002 |
| WO | 2018003900 A1 | 1/2018 |
| WO | 2020013307 A1 | 1/2020 |
| WO | 2022133198 A1 | 6/2022 |
| WO | 2023076874 A1 | 5/2023 |

OTHER PUBLICATIONS

Jungerson et al., "The science behind the probiotic strain *Bifidobaterium animalis* subsp. *lactis* BB-12." Microorganisms, 2, 92-110. ( Year: 2014).*
Saarela et al., "Influence of fermentation time, cryoprotectant and neutralization of cell concentrate on freeze-drying survival, storage stability, and acid and bile exposure of *Bifidobacterium animalis* ssp. *lactis* cells produced without." Journal of Applied Microbiology. 99: 1330-1339. (Year: 2005).*
The First Office Action for Chinese Application No. 202110210084.1, dated Dec. 9, 2021, 20 pages.
The Second Office Action for Chinese Application No. 202110210084.1, dated Mar. 1, 2022, 20 pages.
The First Office Action for Chinese Application No. 202110215103.X, dated Jan. 4, 2022, 14 pages.
The International search report for PCT Application No. PCT/CN2022/085752, dated Jul. 6, 2022, 10 pages.
E. Amanda Bhutto et al. How to effectively educate students with autism spectrum disorder, dated Oct. 31, 2016, 3 pages.
Gil Marie Valle. Entering the Inner World of Children Aged 6-11, dated Jan. 31, 2019, 4 pages.
Shanghai Changning District Population and Family Planning Commission. The Golden Key to Scientific Parenting, dated May 31, 2008, 4 pages.
Qu Wan et al. Effects of Two Probiotics on the Characteristics of Behavior and Intestinal Microbiota of the Depressed Model Rat, Journal of Chinese Institute of Food Science and Technology, vol. 20 No. 12, dated Dec. 25, 2020, 8 pages.
Weizhong Dong et al. *Bifidobacterium animalis* subsp. *lactis* BB-12 Improves the State Anxiety and Sports Performance of Young Divers Under Stress Situations: A Single-Arm, Prospective Proof-of-Concept Study, Frontiers in Psychology, dated Jan. 13, 2021, 10 pages.

(Continued)

*Primary Examiner* — Suzanne M Noakes
*Assistant Examiner* — Ciara A McKnight
(74) *Attorney, Agent, or Firm* — East IP P.C.

(57) ABSTRACT

Provided is a *Bifidobacterium lactis*. The *Bifidobacterium lactis* is *Bifidobacterium animalis* subsp. *lactis* BL-11, and the preservation number of the *Bifidobacterium animalis* subsp. *lactis* BL-11 is CGMCC No. 20847. The provided *Bifidobacterium animalis* subsp. *lactis* can improve intestine metabolism disorder and normalize the composition of intestine microbiome so as to improve height, suppresses obesity, promote infant and youth physical development and mental development, and prevent and treat mental disorders, said mental disorders including anxiety, depression, attention-deficit/hyperactivity disorder, autism, schizophrenia, hepatic encephalopathy, anorexia, Tourette syndrome, and Asperger syndrome.

2 Claims, 15 Drawing Sheets

Specification includes a Sequence Listing.

(56) References Cited

OTHER PUBLICATIONS

Xue-Jun Kong et al. The Effects of Probiotic Supplementation on Anthropometric Growth and Gut Microbiota Composition in Patients With Prader-Willi Syndrome: A Randomized Double-Blinded Placebo-Controlled Trial, Frontiers in Nutrition, vol. 8, dated Feb. 19, 2021, 14 pages.

Sun Shunan et al. The effect of Bifidobacterium lactis on anxiety and depression in patients with Parkinson's disease, Journal of Shenyang Pharmaceutical University, vol. 37 No. 4, dated Apr. 20, 2020, 6 pages.

Zhang darong. Digestive Diseases and Microecology, dated Mar. 31, 2001, 6 pages.

Liu Pei. The mechanism of multiple organ failure in end-stage liver disease, Liaoning Science and Technology Press, dated Jul. 2016, 4 pages.

The Rejection Decision for Chinese Application No. 202110210084. 1, dated May 20, 2022, 9 pages.

The Second Office Action for Chinese Application No. 202110215103. X. dated Mar. 30, 2022, 12 pages.

The First Office Action for the Japanese Application No. 2023-549064, dated Oct. 11, 2024, 8 pages.

The extended European Search Report for the EP Application No. 22752363.6, dated Aug. 29, 2024, 9 pages.

Liu Kevin et al. "Altered Salivary Microbiota Following *Bifidobacterium animalis* Subsp.*lactis*BL-11 Supplementation Are Associated with Anthropometric Growth and Social Behavior Severity in Individuals with Prader-Willi Syndrome", dated Apr. 26, 2022, 13 pages.

Amat-Bou Montse, et al. "Effects of *Bifidobacterium animalis* Subsp.*lactis* (BPL1)Supplementation in Children and Adolescents with Prader-Willi Syndrome: A Randomized Crossover Trial", Oct. 13, 2020, 15 pages.

The First Office Action for the CA Application No. 3208064, dated Aug. 27, 2024, 4 pages.

The Notification of Reexamination dated Oct. 16, 2025 for Chinese Application No. 202110210084.1, 22 pages.

Eicher TP, Mohajeri MH. Overlapping Mechanisms of Action of Brain-Active Bacteria and Bacterial Metabolites in the Pathogenesis of Common Brain Diseases. Nutrients. Jun. 27, 2022;14(13):2661. 51 pages.

Roth FC, Draguhn A. GABA metabolism and transport: effects on synaptic efficacy. Neural Plast. 2012;2012:805830. 12 pages.

Puts NA, Ryan M, Oeltzschner G, Horska A, Edden RAE, Mahone EM. Reduced striatal GABA in unmedicated children with ADHD at 7T. Psychiatry Res Neuroimaging. Jul. 30, 2020;301:111082. 10 pages.

DeMayo MM, Harris AD, Song YJC, Pokorski I, Thapa R, Patel S, Ambarchi Z, Thomas EE, Hickie IB, Guastella AJ. Age-related parietal GABA alterations in children with autism spectrum disorder. Autism Res. May 2021; 14(5):859-872. 14 pages.

" Modern Weight Management System ", edited by the NIAS Nutrition International Training Program, published by Jiangsu Phoenix Science and Technology Press, p. 118, Oct. 2018, 4 pages.

Sun Guiju et al., " Nursing Nutrition" 2nd edition, Southeast University Press, pp. 94-95, Jul. 2020, 8 pages.

"Scientific Management of Daily Life for Children with ADHD" written by Joel T. Nigg and translated by Xiao Fengqiu, published by China Light Industry Press, pp. 72-73, Oct. 2019, 6 pages.

The First Office Action dated Nov. 27, 2025 for Korean Application No. 10-2023-7030867, 17 pages.

Front. Nutr., vol. 8, Atricle No. 587974, pp. 1-14, Feb. 19, 2021, 14 pages.

* cited by examiner

Survival rate (%)

Result of the intestinal
permeability measurement

LPS (U/L)     D-lactic acid (mg/L)

▨ Control  ▨ Probiotics

SEQUENCE LISTING

<160> NUMBER OF SEQ ID NOS: 4

<210> SEQ ID NO 1
<211> LENGTH: 67
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (59)..(59)
<223> OTHER INFORMATION: n is a, g, c or t
<220> FEATURE:
<221> NAME/KEY: misc_feature
<222> LOCATION: (60)..(60)
<223> OTHER INFORMATION: b is g, c or t
<220> FEATURE:
<221> NAME/KEY: misc_feature
<222> LOCATION: (64)..(64)
<223> OTHER INFORMATION: s is g or c

<400> SEQUENCE: 1
tcgtcggcag cgtcagatgt gtataagaga cagcctacgg gaggcagcag cctacgggnb      60 gcascag                                                                67

<210> SEQ ID NO 2
<211> LENGTH: 56
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (42)..(42)
<223> OTHER INFORMATION: n is a, g, c or t
<220> FEATURE:
<221> NAME/KEY: misc_feature
<222> LOCATION: (43)..(43)
<223> OTHER INFORMATION: v is a, g or c

<400> SEQUENCE: 2
gtctcgtggg ctcggagatg tgtataagag acagtgacta cnvgggtatc taatcc         56

<210> SEQ ID NO 3
<211> LENGTH: 17
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: y is c or t
<220> FEATURE:
<221> NAME/KEY: misc_feature
<222> LOCATION: (9)..(9)
<223> OTHER INFORMATION: r is a or g
<220> FEATURE:
<221> NAME/KEY: misc_feature
<222> LOCATION: (10)..(10)
<223> OTHER INFORMATION: b is c, t or g
<220> FEATURE:
<221> NAME/KEY: misc_feature
<222> LOCATION: (14)..(14)
<223> OTHER INFORMATION: s is c or g

<400> SEQUENCE: 3
cctaygggrb gcascag                                                     17

<210> SEQ ID NO 4
<211> LENGTH: 20

-continued

```
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (8)..(8)
<223> OTHER INFORMATION: n is a, c, g or t
<220> FEATURE:
<221> NAME/KEY: misc_feature
<222> LOCATION: (9)..(9)
<223> OTHER INFORMATION: n is a, c, g or t

<400> SEQUENCE: 4
ggactacnng ggtatctaat                                              20
```

BIFIDOBACTERIUM ANIMALIS SUBSP. LACTIS AND USE THEREOF

CROSS REFERENCE TO RELATED APPLICATIONS

This application is a National Stage of International Application No. PCT/CN2022/085752, filed on Apr. 8, 2022, which claims priority to Chinese Patent Application No. 202110185144.9, filed on Feb. 10, 2021 and Chinese Patent Application No. 202110185142.X, filed on Feb. 10, 2021, all of which are hereby incorporated by reference in their entireties.

TECHNICAL FIELD

The present disclosure relates to the technical field of microorganisms, in particular to a *Bifidobacterium animalis* subsp. *lactis* and use thereof.

BACKGROUND

Studies have found that intestinal bacteria can affect the physical development of the host, and some bacteria can mediate the physical development of the host by affecting growth hormone (GH)/insulin-like growth factor-1 (IGF-1). Both germ-free mice and antibiotic-treated mice exhibited reduced growth, which was associated with reduced levels of growth hormone releasing peptide, growth hormone and IGF-1. In addition, in both mice and humans, microbial deficiency leads to maturation and growth restrictions, such as chronic malnutrition, anorexia nervosa, growth retardation, short stature, and even developmental abnormalities of the nervous and immune systems. Insulin-like growth factor 1 (IGF-1), as a hormone with a known effect on bone growth, significantly increases in serum levels as well as in liver and adipose tissue with increasing intestinal microbial colonization. However, after antibiotic treatment, intestinal microbiota is greatly reduced, which can reduce serum IGF-1 and inhibit bone formation. Supplementation with the microbial metabolite short-chain fatty acids (SCFA) after antibiotic treatment restored IGF-1 and bone mass to normal levels. In addition, germ-free mice had lower IGF-1 levels. However, treatment with beneficial microbes modestly increased bone mineral density, increased IGF-1 levels and prevented bone loss. Insulin-like growth factor 1 (IGF-1) is a growth factor that affects endocrine and paracrine/autocrine pathways of bone growth. Exogenous IGF-1 can promote the longitudinal growth of the femur. IGF-1 was observed to affect the maturation of the growth plate and the formation of secondary ossification centers in the absence of chondro-specific insulin-like growth factor I receptor (Igf1r). Liver-specific IGF-1-deficient mice have been found to have a 75% reduction in serum IGF-1 but still exhibit relatively normal physical development, suggesting that local IGF-1 can also promote bone growth. In addition, IGF-1 can promote osteoblasts (including affecting bone formation and bone resorption, respectively). Therefore, the alteration of intestinal microbiota can promote bone formation and resorption, leading to net bone growth, and the microbiota can promote bone growth and remodeling by inducing IGF-1. Short-chain fatty acids (SCFA) produced by direct supplementation of probiotics, prebiotics, or microbial fermentation of cellulose may induce an increase in IGF-1, which in turn affects bone growth and health.

In addition, intestinal microbiota can regulate brain function and behavior through the gut-brain axis. In addition, the intestinal microbiota and the brain communicate bi-directionally through the autonomic nervous system, enteric nervous system, immune system, olfactory system, enteroendocrine signals, neurotransmitters, branched chain amino acids, bile acids, short-chain fatty acids, spinal cord, hypothalamic-pituitary-adrenal axis, peptidoglycan and other pathways and mediators. The bidirectional communication between the intestinal microbiota and the central nervous system, that is microbiota-gut-brain axis, can affect the neurodevelopment and function of animals, thereby affecting social behavior. This bidirectional effect of the microbiota-gut-brain axis is affected by internal factors such as gender and genetics, as well as external factors such as environment, diet, genetics, and stress. Therefore, the intestinal microbiota is involved in the pathogenesis of a variety of nervous system related diseases. At the same time, psychological and behavioral responses can in turn affect the composition or function of the intestinal microbiota. It has been proved that interventions targeting the intestinal microbiota are expected to treat diseases such as anxiety, depression, schizophrenia, ADHD, transient tic disorder, Parkinson's disease, Alzheimer's disease, and social disorders such as autism. For example, attention-deficit/hyperactivity disorder (ADHD), one of the most common neurobehavioral developmental disorder in infant, age-mismatched attention deficit, reduced attention span, excessive activity regardless of occasions, emotional impulsivity, and often accompanied by cognitive impairment, conduct disorder, and learning difficulties, etc. The ADHD has a high incidence, which has a significant negative impact on the academic, family and social life of patients. However, there is still a lack of treatments for ADHD.

Therefore, there is an urgent need to develop a probiotic that can anti-obesity, promote the infant and youth physical development, and prevent and treat mental disorders, which is of great significance for the infant and youth or patients with mental disorders and their families.

SUMMARY

The ASCII plain text file, named "234693USPF00_Sequence_listing" dated Mar. 1, 2024, with the size of the file in 2 KB, which is based on and replacing the Sequence Listing submitted with WIPO on Aug. 18, 2022, is hereby incorporated by reference in its entirety. The present disclosure provides a *Bifidobacterium animalis* subsp. *lactis* and use thereof. The *Bifidobacterium animalis* subsp. *lactis* can improve intestinal metabolic disorder and normalize the composition of intestinal microbiome so as to effectively suppress obesity, promote the infant and youth physical development, and promote their mental development. The *Bifidobacterium animalis* subsp. *lactis* can also effectively improve intestinal permeability and reduce levels of LPS and D-lactic acid in the blood, so as to play a role in the prevention and treatment of a mental disorder. Such mental disorder comprises anxiety, depression, attention-deficit/hyperactivity disorder, autism, autistic disorder, schizophrenia, hepatic encephalopathy, anorexia, Tourette syndrome, and Asperger syndrome.

In order to achieve the above purposes, in a first aspect of the present disclosure, there is provided a *Bifidobacterium animalis* subsp. *lactis*, which is *Bifidobacterium animalis* subsp. *lactis* BL-11, wherein the *Bifidobacterium animalis* subsp. *lactis* BL-11 has an accession number of CGMCC No. 20847.

In a second aspect of the present disclosure, there is provided a *Bifidobacterium animalis* subsp. *lactis* preparation, wherein the preparation is a solid bacterial powder or a liquid beverage, and the *Bifidobacterium animalis* subsp. *lactis* is *Bifidobacterium animalis* subsp. *lactis* described in the first aspect of the present disclosure.

In a third aspect of the present disclosure, there is provided use of the above *Bifidobacterium animalis* subsp. *lactis* in the preparation of a food composition or a pharmaceutical composition for improving intestinal metabolism disorder and promoting the normalization of the composition of intestinal microbiome.

In a fourth aspect of the present disclosure, there is provided use of the above *Bifidobacterium animalis* subsp. *lactis* in the preparation of a food composition or a pharmaceutical composition for suppressing infant and youth obesity.

In a fifth aspect of the present disclosure, there is provided use of the above *Bifidobacterium animalis* subsp. *lactis* in the preparation of a food composition or a pharmaceutical composition for promoting infant and youth physical development.

In a sixth aspect of the present disclosure, there is provided use of the above *Bifidobacterium animalis* subsp. *lactis* in the preparation of a food composition or a pharmaceutical composition for promoting infant and youth height increase.

In a seventh aspect of the present disclosure, there is provided use of the above *Bifidobacterium animalis* subsp. *lactis* in the preparation of a food composition or a pharmaceutical composition for promoting infant and youth mental development.

Optionally, the *Bifidobacterium animalis* subsp. *lactis* BL-11 has a content of 1-25 parts by weight, preferably 1-15 parts by weight, relative to 100 parts by weight of the food composition or the pharmaceutical composition; the *Bifidobacterium animalis* subsp. *lactis* BL-11 is used in a form of live bacteria of the *Bifidobacterium animalis* subsp. *lactis* BL-11, inactivated bacteria of the *Bifidobacterium animalis* subsp. *lactis* BL-11 or extracts from the *Bifidobacterium animalis* subsp. *lactis* BL-11.

Optionally, the *Bifidobacterium animalis* subsp. *lactis* BL-11 has a viable count of $1.0 \times 10^6$-$1.5 \times 10^{12}$ CFU/g, preferably $3.0 \times 10^{10}$-$5.0 \times 10^{11}$ CFU/g.

Optionally, the food composition is one or more of fermented milk, cheese, milk containing beverage, solid beverage, and milk powder.

Optionally, the *Bifidobacterium animalis* subsp. *lactis* BL-11 is administered at a dose of $2.0 \times 10^6$-$1.5 \times 10^{11}$ CFU/kg/day, preferably $3.0 \times 10^4$-$8.0 \times 10^{10}$ CFU/kg/day, based on a weight of a human body.

In an eighth aspect of the present disclosure, there is provided use of the above *Bifidobacterium animalis* subsp. *lactis* in the preparation of a food composition or a pharmaceutical composition for preventing and treating a mental disorder.

Optionally, the mental disorder comprises anxiety, depression, attention-deficit/hyperactivity disorder, autism, autistic disorder, schizophrenia, hepatic encephalopathy, anorexia, Tourette syndrome, and Asperger syndrome.

Optionally, the food composition or the pharmaceutical composition further comprises one or more of skimmed milk powder, trehalose, fructooligosaccharide, lactose, glucose, sucrose, L-sodium ascorbate, L-malic acid, and L-lactic acid.

Optionally, the food composition or the pharmaceutical composition further comprises a flavoring agent, a sweetener, a thickener, a stabilizer, a surfactant, a lubricant, an acid neutralizing agent, a dispersant, a buffer solution or a buffer, a debitterizing agent, pH stabilizer, a preservative, a desugaring agent and/or a coloring agent, such as, lactitol, sorbitol, maltitol, aspartame, *Stevia rebaudiana*, siraitia grosvenorii, sucralose, xylitol, vanilla, chocolate, fruit flavors, artificial flavors, or a mixture or combination thereof.

Optionally, the food composition or the pharmaceutical composition further comprises a vitamin, a mineral and/or a dietary supplement or a prebiotic nutrient, or at least one prebiotic, wherein, optionally, the prebiotic comprises inulin, artichoke extract, chicory root extract, jerusalem artichoke root extract, fructooligosaccharide, galactooligosaccharide, isomalto-oligosaccharide, xylooligosaccharide, stachyose, mannose oligosaccharide, arabinose oligosaccharide, resistant dextrin, resistant starch, or a mixture or combination thereof.

Optionally, wherein the food composition or the pharmaceutical composition further comprises ubiquinone (CoQ10), lycopene, β-carotene, tryptophan, vitamin B6, vitamin B12, or a mixture or combination thereof.

Optionally, the food composition or pharmaceutical composition further comprises probiotics, wherein, optionally, the probiotics comprise microorganisms or bacteria or bacterial components that are cultured or extracted from faeces, and optionally, the bacteria or bacterial components comprise or are derived from *Lactobacillus, Bifidobacterium, Escherichia coli* (*E. coli*), *Prevotella, Faecalibacterium, Blautia*, Bacteroidetes, Firmicutes, and an equivalent, or a mixture or combination thereof.

Optionally, the *Bifidobacterium animalis* subsp. *lactis* BL-11 has a content of 0.5-20 parts by weight, preferably 1-15 parts by weight, relative to 100 parts by weight of the food composition or the pharmaceutical composition; the *Bifidobacterium animalis* subsp. *lactis* BL-11 is used in a form of live bacteria of the *Bifidobacterium animalis* subsp. *lactis* BL-11, inactivated bacteria of the *Bifidobacterium animalis* subsp. *lactis* BL-11 or extracts from the *Bifidobacterium animalis* subsp. *lactis* BL-11; and the *Bifidobacterium animalis* subsp. *lactis* BL-11 has a viable count of $1.0 \times 10^6$-$1.5 \times 10^{12}$ CFU/g, preferably $3.0 \times 10^{10}$-$5.0 \times 10^{11}$ CFU/g.

Optionally, the food composition is one or more of fermented milk, cheese, milk containing beverage, solid beverage, and milk powder.

Optionally, the *Bifidobacterium animalis* subsp. *lactis* BL-11 is administered at a dose of $2.0 \times 10^9$-$1.5 \times 10^{11}$ CFU/kg/day, preferably $3.0 \times 10^4$-$8.0 \times 10^{10}$ CFU/kg/day, based on a weight of a human body.

Optionally, different forms of delivery and vectors are used. The food composition or the pharmaceutical composition may be a powder, a tablet, a liquid, a gum, a soft candy, a tablet candy, a yogurt, a milk, a cheese, an ice cream, a frozen food, a health food, a drug, or a feed.

The *Bifidobacterium animalis* subsp. *lactis* BL-11 of the present disclosure can improve intestinal permeability and reduce levels of LPS and D-lactic acid in the blood.

The *Bifidobacterium animalis* subsp. *lactis* BL-11 of the present disclosure can be used to promote autonomous active activity, improve the memory function of disposable avoidance response, and improve anhedonia caused by stress stimuli.

Through the above technical solutions, probiotics provided in the present disclosure can effectively improve intestinal metabolic disorder and normalize the composition of intestinal microbiome, promote the infant and youth physical development, and can improve intestinal permeability and reduce levels of LPS and D-lactic acid in the blood, so as to play a role in the prevention and treatment of a mental disorder. Such mental disorder comprises anxiety, depression, attention-deficit/hyperactivity disorder, autism, autistic disorder, schizophrenia, hepatic encephalopathy, anorexia, Tourette syndrome, and Asperger syndrome.

Other features and advantages of the present disclosure will be detailed in the following specific embodiments.

Biological Material Deposit Information

*Bifidobacterium animalis* subsp. *lactis* BL-11, classified as *Bifidobacterium animalis* subsp. *lactis*, was deposited at China General Microbiological Culture Collection Center (CGMCC, Address: NO. 1 Beichen West Road, Chaoyang District, Beijing 100101, China; Institute of Microbiology, Chinese Academy of Sciences) on Oct. 10, 2020, and it was assigned accession number CGMCC No. 20847.

DESCRIPTION OF THE DRAWINGS

The drawings are provided to provide a further understanding of the present disclosure and form part of the specification, together with the specific embodiments below, for the interpretation of the present disclosure, but do not constitute a limitation of the present disclosure. In the drawings.

DETAILED DESCRIPTION

Figure 1:
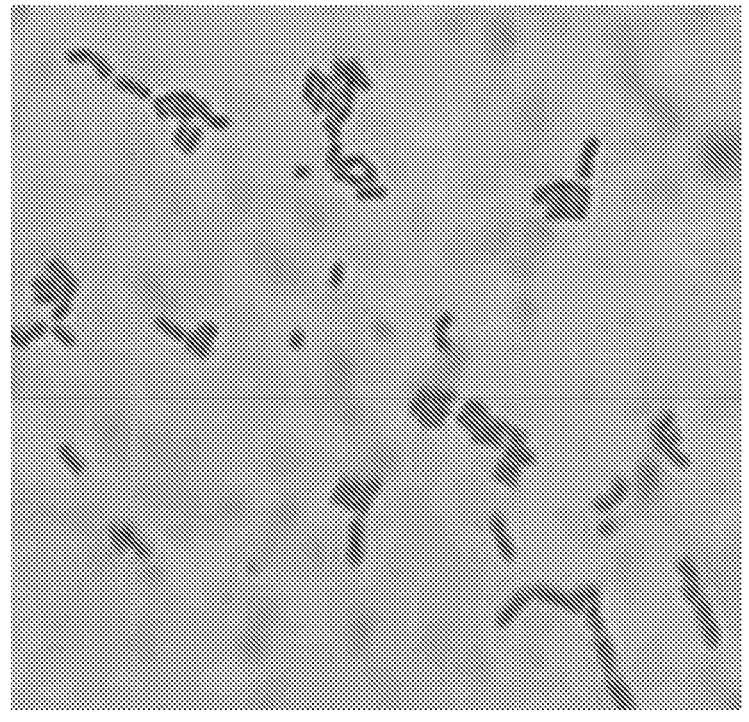
FIG. 1 shows an image of *Bifidobacterium animalis* subsp. *lactis* BL-11 observed by microscope.

Hereinafter, specific embodiments of the present disclosure will be described in detail, in combination with the drawings. It should be understood that the specific embodiments described herein are intended only to illustrate and explain the present disclosure, but not intended to limit the present disclosure.

In a first aspect of the present disclosure, there is provided a *Bifidobacterium animalis* subsp. *lactis*, which is *Bifidobacterium animalis* subsp. *lactis* BL-11, wherein the *Bifidobacterium animalis* subsp. *lactis* BL-11 has an accession number of CGMCC No. 20847.

In a second aspect of the present disclosure, there is provided a *Bifidobacterium animalis* subsp. *lactis* preparation, wherein the preparation is a solid bacterial powder or a liquid beverage, and the *Bifidobacterium animalis* subsp. *lactis* is *Bifidobacterium animalis* subsp. *lactis* described in the first aspect of the present disclosure.

In a third aspect of the present disclosure, there is provided use of the above *Bifidobacterium animalis* subsp. *lactis* in the preparation of a food composition or a pharmaceutical composition for improving intestinal metabolism disorder and promoting the normalization of the composition of intestinal microbiome.

In a fourth aspect of the present disclosure, there is provided use of the above *Bifidobacterium animalis* subsp. *lactis* in the preparation of a food composition or a pharmaceutical composition for suppressing infant and youth obesity.

In a fifth aspect of the present disclosure, there is provided use of the above *Bifidobacterium animalis* subsp. *lactis* in the preparation of a food composition or a pharmaceutical composition for promoting infant and youth physical development.

In a sixth aspect of the present disclosure, there is provided use of the above *Bifidobacterium animalis* subsp. *lactis* in the preparation of a food composition or a pharmaceutical composition for promoting infant and youth height increase.

In a seventh aspect of the present disclosure, there is provided use of the above *Bifidobacterium animalis* subsp. *lactis* in the preparation of a food composition or a pharmaceutical composition for promoting infant and youth mental development.

Optionally, the *Bifidobacterium animalis* subsp. *lactis* BL-11 has a content of 1-25 parts by weight, preferably 1-15 parts by weight, relative to 100 parts by weight of the food composition or the pharmaceutical composition; the *Bifidobacterium animalis* subsp. *lactis* BL-11 is used in a form of live bacteria of the *Bifidobacterium animalis* subsp. *lactis* BL-11, inactivated bacteria of the *Bifidobacterium animalis* subsp. *lactis* BL-11 or extracts from the *Bifidobacterium animalis* subsp. *lactis* BL-11.

Optionally, the *Bifidobacterium animalis* subsp. *lactis* BL-11 has a viable count of $1.0\times10^6$-$1.5\times10^{12}$ CFU/g, preferably $3.0\times10^{10}$-$5.0\times10^{11}$ CFU/g.

Optionally, the food composition is one or more of fermented milk, cheese, milk containing beverage, solid beverage, and milk powder.

Optionally, the *Bifidobacterium animalis* subsp. *lactis* BL-11 is administered at a dose of $2.0\times10^6$-$1.5\times10^{11}$ CFU/kg/day, preferably $3.0\times10^4$-$8.0\times10^{10}$ CFU/kg/day, based on a weight of a human body.

In an eighth aspect of the present disclosure, there is provided use of the above *Bifidobacterium animalis* subsp. *lactis* in the preparation of a food composition or a pharmaceutical composition for preventing and treating a mental disorder.

Optionally, the mental disorder comprises anxiety, depression, attention-deficit/hyperactivity disorder, autism, autistic disorder, schizophrenia, hepatic encephalopathy, anorexia, Tourette syndrome, and Asperger syndrome.

Optionally, the food composition or the pharmaceutical composition further comprises one or more of skimmed milk powder, trehalose, fructooligosaccharide, lactose, glucose, sucrose, L-sodium ascorbate, L-malic acid, and L-lactic acid.

Optionally, the food composition or the pharmaceutical composition further comprises a flavoring agent, a sweetener, a thickener, a stabilizer, a surfactant, a lubricant, an acid neutralizing agent, a dispersant, a buffer solution or a buffer, a debitterizing agent, pH stabilizer, a preservative, a desugaring agent and/or a coloring agent, such as, lactitol, sorbitol, maltitol, aspartame, *Stevia rebaudiana*, siraitia grosvenorii, sucralose, xylitol, vanilla, chocolate, fruit flavors, artificial flavors, or a mixture or combination thereof.

Optionally, the food composition or the pharmaceutical composition further comprises a vitamin, a mineral and/or a dietary supplement or a prebiotic nutrient, or at least one prebiotic, wherein, optionally, the prebiotic comprises inulin, artichoke extract, chicory root extract, jerusalem artichoke root extract, fructooligosaccharide, galactooligosaccharide, isomalto-oligosaccharide, xylooligosaccharide, stachyose, mannose oligosaccharide, arabinose oligosaccharide, resistant dextrin, resistant starch, or a mixture or combination thereof.

Optionally, wherein the food composition or the pharmaceutical composition further comprises ubiquinone (CoQ10), lycopene, β-carotene, tryptophan, vitamin B6, vitamin B12, or a mixture or combination thereof.

Optionally, the food composition or pharmaceutical composition further comprises probiotics, wherein, optionally, the probiotics comprise microorganisms or bacteria or bacterial components that are cultured or extracted from faeces, and optionally, the bacteria or bacterial components comprise or are derived from *Lactobacillus, Bifidobacterium, Escherichia coli (E. coli), Prevotella, Faecalibacterium,* Blautia, Bacteroidetes, Firmicutes, and an equivalent, or a mixture or combination thereof.

Optionally, the *Bifidobacterium animalis* subsp. *lactis* BL-11 has a content of 0.5-20 parts by weight, preferably 1-15 parts by weight, relative to 100 parts by weight of the food composition or the pharmaceutical composition; the *Bifidobacterium animalis* subsp. *lactis* BL-11 is used in a form of live bacteria of the *Bifidobacterium animalis* subsp. *lactis* BL-11, inactivated bacteria of the *Bifidobacterium animalis* subsp. *lactis* BL-11 or extracts from the *Bifidobacterium animalis* subsp. *lactis* BL-11; and the *Bifidobacterium animalis* subsp. *lactis* BL-11 has a viable count of $1.0\times10^6$-$1.5\times10^{12}$ CFU/g, preferably $3.0\times10^{10}$-$5.0\times10^{11}$ CFU/g.

Optionally, the food composition is one or more of fermented milk, cheese, milk containing beverage, solid beverage, and milk powder.

Optionally, the *Bifidobacterium animalis* subsp. *lactis* BL-11 is administered at a dose of $2.0\times10^9$-$1.5\times10^{11}$ CFU/kg/day, preferably $3.0\times10^4$-$8.0\times10^{10}$ CFU/kg/day, based on a weight of a human body.

Optionally, different forms of delivery and vectors are used. The food composition or the pharmaceutical composition may be a powder, a tablet, a liquid, a gum, a soft candy, a tablet candy, a yogurt, a milk, a cheese, an ice cream, a frozen food, a health food, a drug, or a feed.

The *Bifidobacterium animalis* subsp. *lactis* BL-11 of the present disclosure can improve intestinal permeability and reduce levels of LPS and D-lactic acid in the blood.

The *Bifidobacterium animalis* subsp. *lactis* BL-11 of the present disclosure can be used to promote autonomous active activity, improve the memory function of disposable avoidance response, and improve anhedonia caused by stress stimuli.

Hereinafter, the present disclosure is further described below by examples, but is not thereby limited in any way.

Example 1

This example is used to illustrate *Bifidobacterium animalis* subsp. *lactis* BL-11 and its performance characteristics.

1. Taxonomic characteristics of *Bifidobacterium animalis* subsp. *lactis* BL-11:

*Bifidobacterium animalis* subsp. *lactis* BL-11 was observed under a microscope, and the results are shown in FIG. 1. The results of the physical and chemical tests are shown in Tables 1 and 2.

TABLE 1

| | Basic information of bacteria | | | | | | | |
|---|---|---|---|---|---|---|---|---|
| | Gram's stain | Spore | Movement | Catalase | Oxidase | Oxygen | $H_2O_2$ | Optimum temperature |
| Result | + | − | − | − | − | − | − | 37° C. |

TABLE 2

| | Ribose | Trehalose | Xylose | Maltose | Lactose | Raffinose | Inulin | Starch | Mannose | Melibiose |
|---|---|---|---|---|---|---|---|---|---|---|
| Result | + | − | + | + | + | + | + | + | − | + |

| | Melezitose | Galactose | Fructose | Cellobiose | Sucrose | L-arabinose | Gluconate sodium | Mannitol | Sorbitol | Salicin |
|---|---|---|---|---|---|---|---|---|---|---|
| Result | − | + | − | − | + | − | − | − | − | + |

Measurement of metabolic capacity of carbohydrate

+ indicates metabolizable; − indicates nonmetabolizable.

2. Tolerance of Artificial Gastric Fluid and Intestinal Fluid of *Bifidobacterium animalis* Subsp. *lactis* BL-11:

*Bifidobacterium* is a genus of bacteria that are not usually acid-fast. In this example, the tolerance of the artificial gastric fluid and intestinal fluid of *Bifidobacterium animalis* subsp. *lactis* BL-11 of the present invention was tested, and at the same time, the currently stored *Bifidobacterium animalis* subsp. *lactis* Bb-XX which has excellent acid resistance and can survive in the gastrointestinal tract was used as a control.

The survival rate of strain BL-11 in artificial gastric fluid (pH=3) was shown in Table 3. The viable survival rate of strain Bb-XX in artificial gastric fluid was 44.7% at 1 hour of treatment and 29.5% at 3 hours of treatment. However, *Bifidobacterium animalis* subsp. *lactis* BL-11 of the present invention had a viable survival rate of 86.2% at 1 hour of treatment and 39.5% at 3 hours of treatment. These results indicates that *Bifidobacterium animalis* subsp. *lactis* BL-11 of the present invention has relatively good gastric acid tolerance, and most of it can successfully pass through the stomach to the intestine to play a probiotic role.

The survival test results of the strain BL-11 in artificial intestinal fluid (pH=8) was shown in Table 3. The data showed that the survival rate of live bacteria of strain Bb-XX in artificial intestinal fluid (pH=8) was 66.1% at 1 hour of treatment. However, the survival rate of *Bifidobacterium animalis* subsp. *lactis* BL-11 in artificial intestinal fluid was 67.5% at 1 hour of treatment, and the survival rates of the two strains were 49.4% and 32.1% after 3 hours of treatment, respectively.

Figure 2:
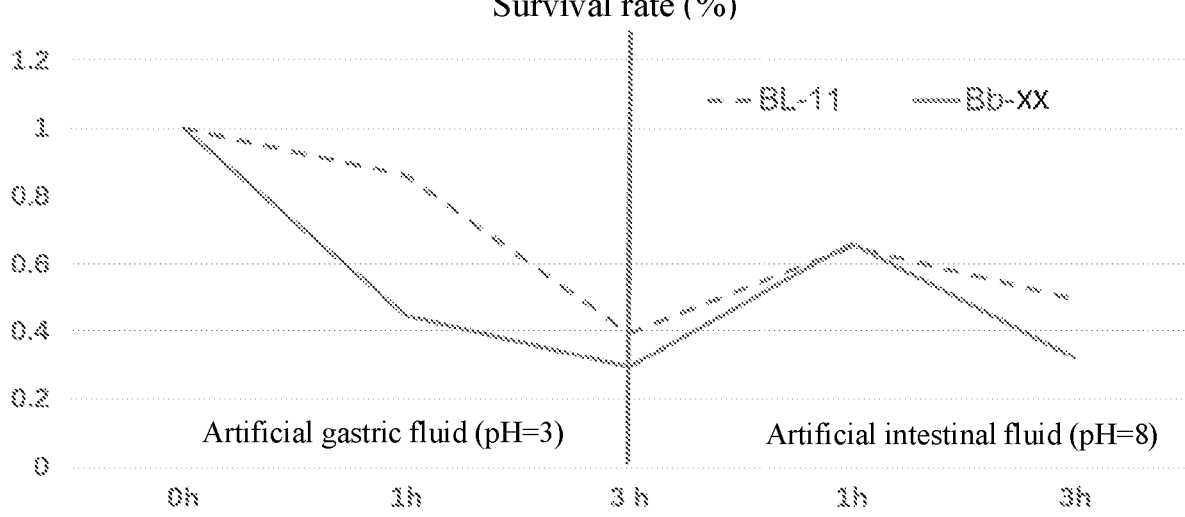
FIG. 2 shows the survival rate of *Bifidobacterium animalis* subsp. *lactis* BL-11 in artificial gastric fluid (pH=3) and artificial intestinal fluid (pH=8).

The above results showed that *Bifidobacterium animalis* subsp. *lactis* BL-11 can still have a good survival rate after digestion with artificial gastric fluid and intestinal fluid (FIG. 2). The *Bifidobacterium animalis* subsp. *lactis* BL-11 of the present invention has better ability to tolerate digestive fluid than the control bacteria, and can survive and colonize in the intestinal tract smoothly.

TABLE 3

| | Test conditions | | | | |
|---|---|---|---|---|---|
| | Artificial gastric fluid (pH = 3) | | | Artificial intestinal fluid (pH = 8) | |
| $10^9$ CFU/mL | 0 h | 1 h | 3 h | 1 h | 3 h |
| BL-11 | 2.1 | 1.81 | 0.83 | 0.56 | 0.41 |
| Bb-XX | 1.9 | 0.85 | 0.56 | 0.37 | 0.18 |

3. Toxicity Test and Safety Detection of *Bifidobacterium animalis* Subsp. *lactis* BL-11:

The *Bifidobacterium animalis* subsp. *lactis* BL-11 of the present invention was inoculated into MRS Liquid medium and cultured anaerobically at 37° C. for 48 hours. The viable count of the *Bifidobacterium animalis* subsp. *lactis* BL-11 in the culture medium was 3.7×10⁹ CFU/mL. The culture stock solution was orally administered to the mice at a dose of 20.0 mL/kg body weight by gavage for 3 consecutive days, after which the mice were observed for an additional 7 days. Healthy male BALB/C mice, aged 6-8 weeks old, and weighted 16-18 g, were fed and watered adlibitum at room temperature (25±2° C.), relative humidity (55±2) %, and 12 h/12 h light/dark. The results showed that compared with the control group, the group treated with the culture stock solution of *Bifidobacterium animalis* subsp. *lactis* BL-11 shows no toxic reaction or death, and there was no significant difference in the weight gain of mice between the two groups (p>0.05).

The antibiotic sensitivity of *Bifidobacterium animalis* subsp. *lactis* BL-11 was evaluated by SN/T 1944-2007 "Determination of bacterial resistance in animals and their products". The evaluation results showed that, the *Bifidobacterium animalis* subsp. *lactis* BL-11 was positive for Ampicillin, penicillin G, Erythromycin, Chloramphenicol, Clindamycin, Vancomycin and Tetracycline, etc, which met the requirements of the European Food Safety Authority (EFSA) standard for the evaluation of resistance of edible bacteria. The *Bifidobacterium animalis* subsp. *lactis* BL-11 does not contain exogenous antibiotic resistance genes and is safe to eat.

Example 2

This example is used to illustrate the functional characteristics of *Bifidobacterium animalis* subsp. *lactis* in promoting physical development.

Microbiota promotes bone formation as well as resorption, resulting in net bone growth. The microbiota induces hormone-like insulin growth factor 1 (IGF-1), which promotes bone growth and remodeling. Short-chain fatty acids (SCFA) produced by microbial fermentation of cellulose also induce IGF-1, suggesting a mechanism by which microbial flora affects bone health.

Female BALB/c mice, aged two month old, were treated with antibiotics and probiotics and maintained under SPF conditions. 30 mice were combined and randomly assigned to treatment groups to minimize cage effects.

The mice were treated with the drinking water mixed with antibiotic mixture for 2 weeks to consume microorganisms, and then the mice were divided into three groups with 10 mice in each group. One group was fed normally as a control group (CK group), and the other two groups were fed with water mixed with probiotics BL-11 or Bb-XX as probiotic groups (including BL-11 or Bb-XX group). The mice in the three groups were fed for four weeks. 3% (g/100 mL) sucrose was added to water in all groups to ensure palatability, as specified in the animal facility. The aqueous solution was freshly prepared and changed twice a week.

After four weeks, mice were sacrificed, and serum was then prepared from blood samples collected by cardiac puncture using a serum separator tube, and the murine IGF-1 standard ABTS ELISA development kit (PeproTech) was used.

Figure 3:
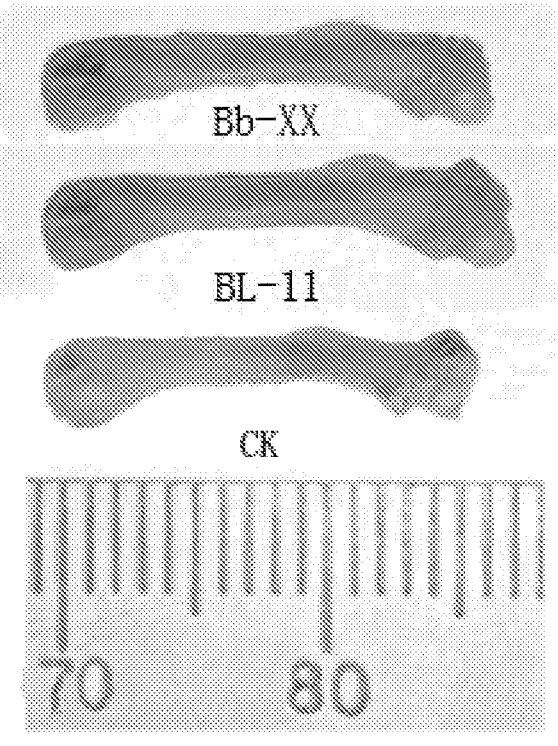
FIGS. 3 and 4 show femur length of mice treated with antibiotics and probiotics.
Figure 4:
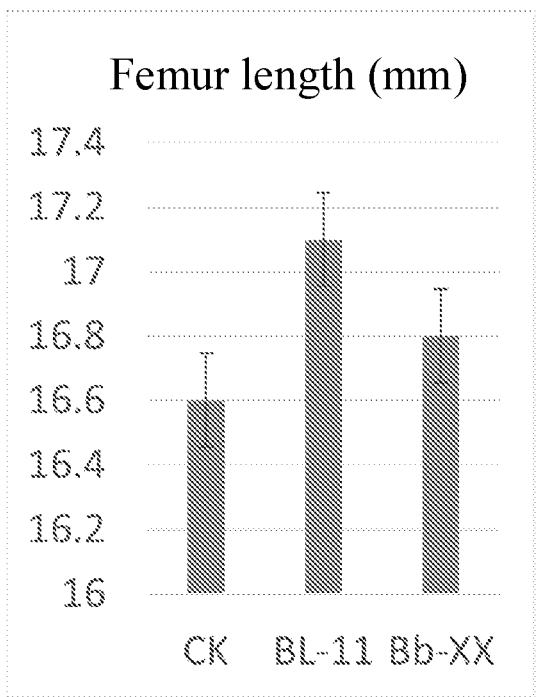

The femur lengths of mice in CK, BL-11 and BB-XX-groups are shown in FIG. 4, and the shank lengths are shown in FIG. 3. There was a significant difference in shank lengths of mice between BL-11 and CK groups (P<0.05). There was no significant difference in shank lengths of mice between BB-XX and CK groups (P<0.05). Data are shown as mean±SD, and t-test was used to determine whether the difference was significant. *P<0.05; P<0.01; *P<0.001.

Figure 5:
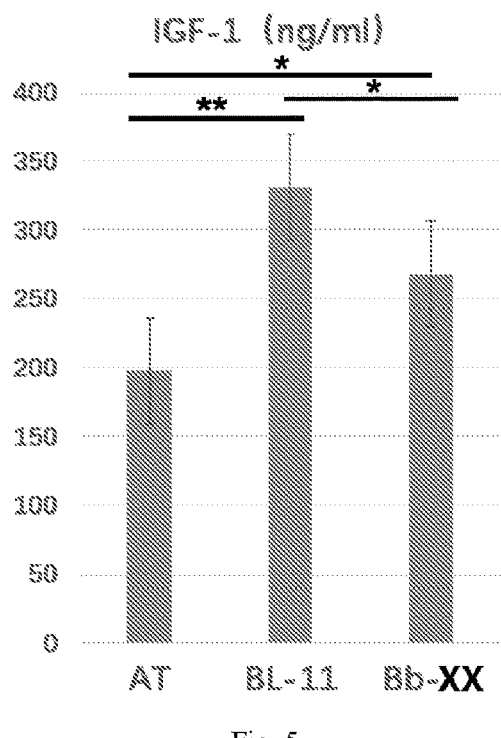
FIG. 5 shows shank length of mice treated with antibiotics and probiotics.
Figure 6:
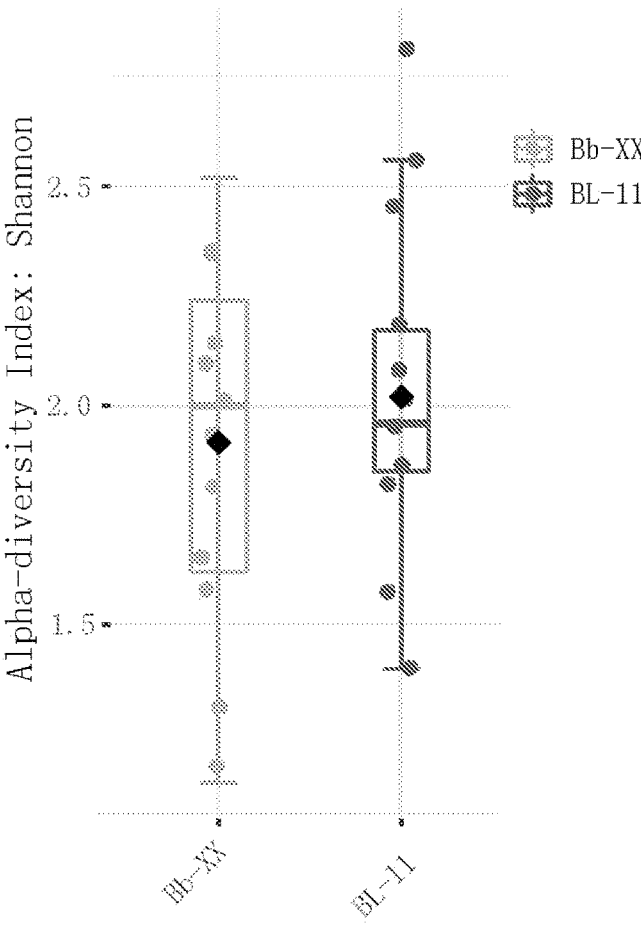
FIG. 6 shows changes in diversity of intestinal microbiota in mice treated with two probiotics.
Figure 7:
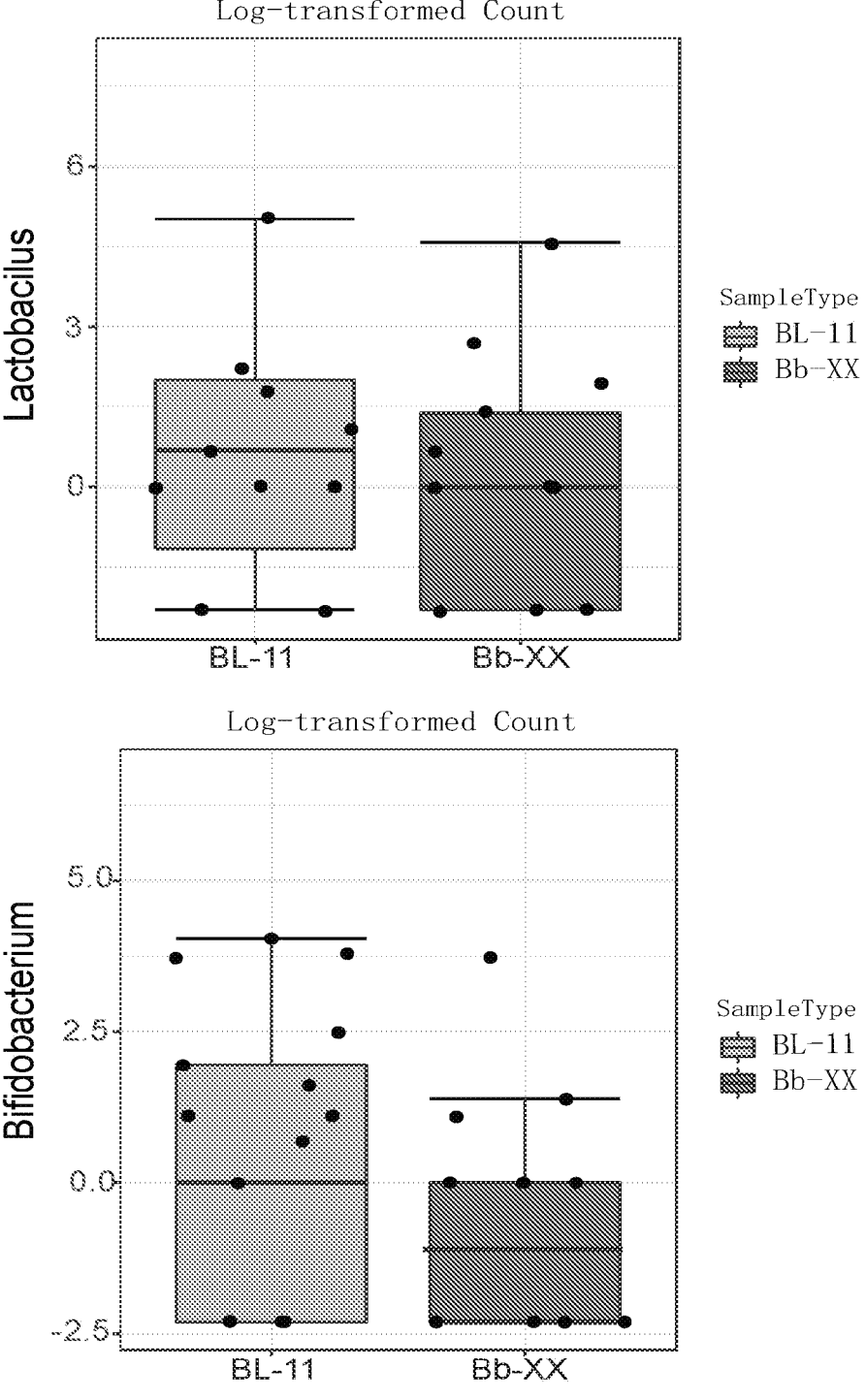
FIG. 7 shows ratios of Bifidobacteria and *Lactobacillus* in the intestine of mice treated with two probiotics.

Analysis of growth regulatory activity: Both germ-free mice and antibiotic-treated mice exhibited reduced growth, reduced levels of growth hormone releasing peptide, growth hormone and IGF-1, and disordered intestinal microbes, leading to growth restriction in mice. The serum IGF-1 levels of the mice treated with antibiotics and then treated with probiotics were measured. Results are shown in FIG. 5, and show that the serum IGF-1 levels of the mice treated with antibiotics and then treated with probiotics were increased. BL-11 can significantly increase the serum IGF-1 levels of the mice (P<0.01), than, and the effect of BL-11 was higher than that of Bb-XX. Diversity of intestinal microbiota: a diversity index analysis showed that there was no significant difference in diversity index between BL-11 and Bb-XX groups. BL-11 group has a slightly higher Shannon index than Bb-XX group, but failed to achieve significant difference (P>0.05), and the results are shown in FIG. 6. The analysis of the two beneficial bacteria in the intestine of mice in the two groups showed that the use of BL-11 could significantly increase a ratio of Bifidobacteria to *Lactobacillus* in the intestine, and the results are shown in FIG. 7.

Figure 8:
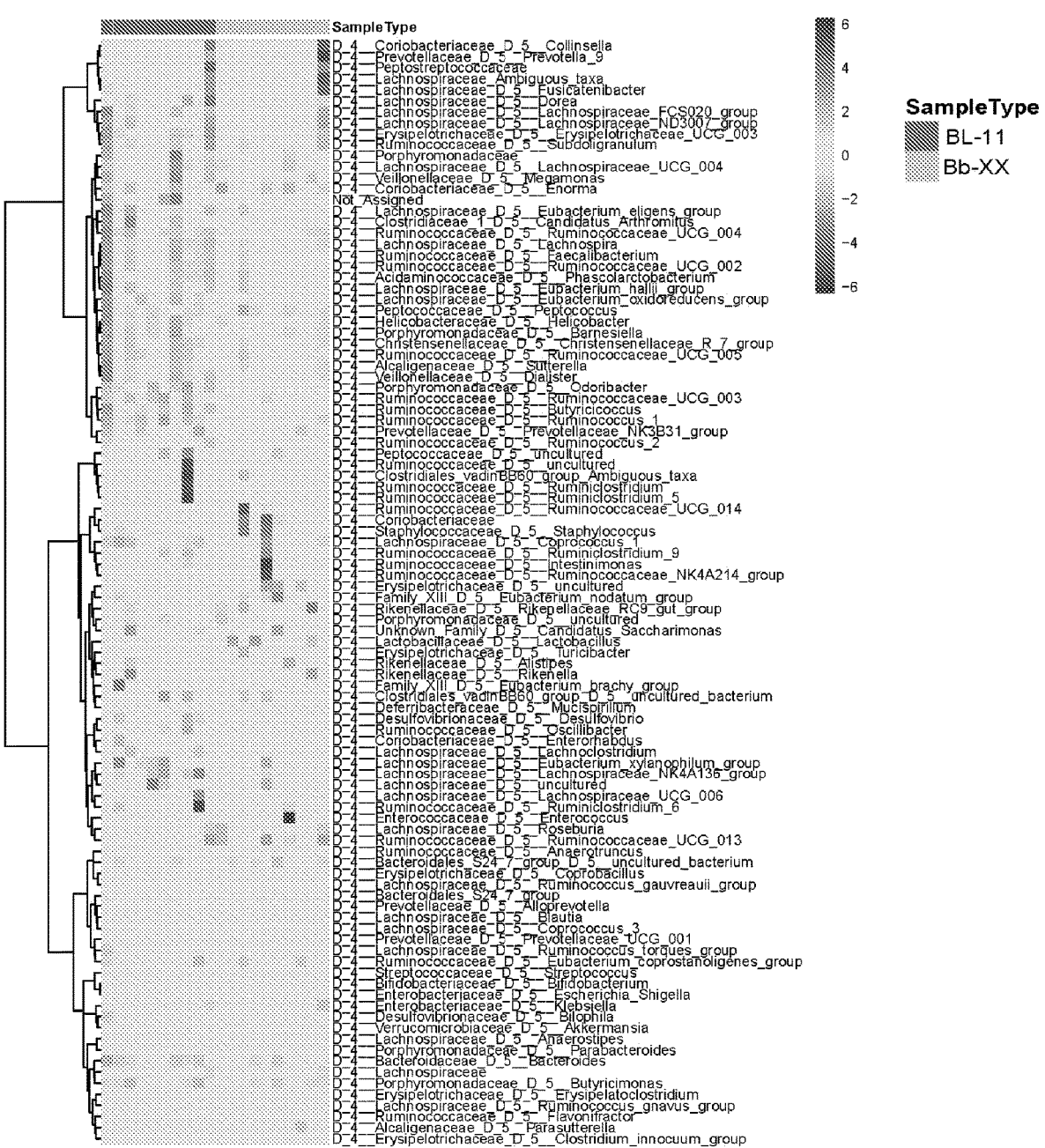
FIG. 8 shows a heat map analysis of intestinal microbiota composition in mice treated with two probiotics.

Heat map analysis (FIG. 8) shows that at the genus level, *Faecalibacterium*, Lachnospira, Lachnospiraceae_UCG_004, Sutterella were increased in the BL-11 group. The increase of these bacteria may be related to the increase of IGF-11 in serum.

Example 3

This example is used to illustrate the preparation of BL-11 bacterial powder and its use in the production of food.

*Bifidobacterium animalis* subsp. *lactis* BL-11 provided in the present invention was cultured anaerobically in MRS Broth liquid medium. After primary culture, secondary culture and expanded culture, the fermentation broth was incubated at 37° C. for 24 hours, centrifuged at 4° C. and 3000 rpm for 10 minutes, the bacteria were collected, washed with phosphate buffer solution (PBS), freeze-dried with skimmed milk, and stored below −20° C.

The BL-11 bacterial powder prepared in this example may be used for foods, drugs, health products or animal feeds.

The food can be fermented milk, cheese, milk containing beverage, solid beverage, milk powder and other common food or health food. Preferably, in the food, the suggested dose of *Bifidobacterium animalis* subsp. *lactis* BL-11 for human use may be $1.0\times10^3$-$1.0\times10^{10}$ CFU/kg body weight/day, more preferably $1.0\times10^4$-$1.0\times10^9$ CFU/kg body weight/day.

Example 4

This example is used to illustrate functional characteristics of promoting physical development in human clinical research.

Subjects and recruitment: 65 patients with Prader-Willi syndrome aged 11 months to 16 years were openly recruited and randomly assigned to two groups treated with probiotics or placebo to perform a 12-week randomized, double-blind, placebo-controlled experiment.

Inclusion criteria: patients with genetically confirmed PWS, without taking any form of probiotics within four weeks, taking a stable drug for at least four weeks; with no planned pharmacologic or psychological interventions during the experiment, willing to provide fecal samples in a timely manner, willing to participate in the study and interview process and without other genetic diseases, pregnancy or breastfeeding conditions. Written informed consent was obtained from the parents or legal guardians of the subjects, as required by the IRB, for the study protocol, which was conducted in accordance with the Declaration of Helsinki.

Methods: Randomized and blinded testing: A randomized, double-blind, placebo controlled design was used. Subjects was randomly assigned and concealed them by a statistician who was not part of the team, so that each unidentified subject generated a random sample number. The coded probiotic and placebo with the same appearance were provided by BEIJING HUAYUAN BIOTECHNOLOGY RES INSTITUTE, to ensure that allocation was concealed and blind spots were maintained. These patients were randomly assigned to receive daily strip bags of the probiotic *Bifidobacterium animalis* subsp. *lactis* BL-11 ($6\times10^{10}$ CFU) or placebo. Body weight, height, ASQ-3, ABC, SRS-2 and CGI-1 were compared between the two groups at 6 and 12 weeks of treatment. The CGI comprises two single-item measurements that assess: (a) psychopathology severity from 1 to 7 (CGI-S) and (b) change in symptoms before and after treatment assessed on a seven-point scale from start to end (CGI-I).

Materials: The probiotic group is treated with powder *Bifidobacterium animalis* subsp. *lactis* BL-11 in the form of strip bag. Each bag of *Bifidobacterium animalis* subsp. *lactis* supplement contained $3\times10^{10}$ colony-forming units (CFU). Placebo was maltodextrin in the same bag as the strip bag of *Bifidobacterium animalis* subsp. *lactis*, similar in color, taste, and flavor to the strip bag of *Bifidobacterium animalis* subsp. *lactis*. Subjects received a bag of *Bifidobacterium animalis* subsp. *lactis* or placebo orally with water twice daily for 12 weeks. As a supplement, maltodextrin had minimal side effects, and as a placebo, maltodextrin also had minimal adverse effects.

Measurement of Primary Outcome:
1. Weight and height were measured by parents using a standard scale and collected by the investigators. Weight, height, and BMI were converted to z scores using age gain provided by the WHO as a reference.
2. Psychological test:
   (1) Age and Stage Questionnaire, third edition (ASQ-3). ASQ-3 is one of the most widely used tools for screening infant and youth development and has five dimensions: communication, total motivation, fine motivation, problem solving, and personal socialization. The total score of the subjects was calculated according to the five dimensions to evaluate the effect of the experiment.
   (2) Aberrant Behavior Checklist (ABC). ABC is a scale for assessing 58 behaviors, and used to measure behavioral problems across five subscales: irritability, lethargy/social withdrawal, stereotypical behavior, hyperactivity/nonconforming behavior, and inappropriate speech. The total score of the subjects was calculated according to the above behavioral problems to evaluate the effect of the experiment.

(3) Social Responsiveness Scale (SRS). SRS contains 65 items and is used to quantitatively assess the severity of social behaviors. The total score of the subjects was calculated according to the above social behaviors, to evaluate the effect of the experiment.

(4) Restrictive and repetitive behaviors (RRB) based on a 4-point scale (0-3) adopted by Gilliam Autism Rating Scale, Third Edition (GARS-3). The total score of the subjects was calculated according to the above behaviors to evaluate the effect of the experiment.

Measurement of Secondary Outcome:

1. Fecal microbiome (1) Sample Processing and Collection

Fecal samples were collected with DNA/RNA shielded fecal collection tubes (Zymo, Cat #R1101) containing 1 mL of preservation solution, transported to the laboratory by ice pack, and then frozen at −80° C. DNA was extracted using the TIANmap fecal DNA kit (TIANGEN™, catalog number DP328) according to the manufacturer's instructions, and DNA samples were carefully quantified using a Nanodrop spectrophotometer. The A260/A280 ratio was measured to confirm the yield of highly purified DNA. The DNA samples were frozen at −20° C. for use.

(2) Sequencing of 16S rRNA Amplicon 16S rRNA V3-V4 libraries were constructed by two rounds of PCR using the following primers:

```
341 F:
                                    (SEQ ID NO. 1)
5'-TCGTCGGCAGCGTCAGATGTGTATAAGAGACAGCCTACGGG

AGGCAGCAGCCTACGGGNBGCASCAG-3'

805 R:
                                    (SEQ ID NO. 2)
5'-GTCTCGTGGGCTCGGAGATGTGTATAAGAGACAGTGACTAC

NVGGGTATCTAATCC-3'
```

The PCR reaction (95° C. for 2 min, followed by 25 cycles of 95° C. for 30 s, 55° C. for 30 s, and 72° C. for 30 s) was performed, followed by a final extension at 72° C. for 5 min. The PCR product was purified with 1×KAPA AMPure (KAPA, catalog number KK8002). Then, the product was subjected to a second PCR reaction step (95° C. for 2 min, followed by eight cycles of 95° C. for 30 s, 55° C. for 30 s and 72° C. for 30 s, and finally extension at 72° C. for 5 min). PCR products were purified by 1×KAPA AMPure and quantified by real-time PCR using the Bioanalyzer DNA kit.

2. Clinical Global Impression (CGI) was developed for use in clinical trials to provide a brief independent assessment of the clinician's perception of overall patient function before and after initiation of the studied drug. The CGI includes two concomitant single-item measurements that assess: (a) psychopathology severity from 1 to 7 (CGI-S) and (b) change from treatment initiation on a similar seven-point scale (CGI-I).

3. Gastrointestinal symptoms were assessed on the basis of the total number of GI symptoms including constipation, diarrhea, abdominal pain, flatulence, hematochezia, nausea, dysphagia, loss of appetite, dyspepsia, and acid regurgitation, at baseline.

Data Analysis

All raw data were recorded and processed in Microsoft™ Excel 2007 and R. Data shown results for reporting double-blind randomized clinical placebo-controlled experiment according to CONSORT recommendations. Statistical procedures were performed using α=0.05 as a significance level. The present invention uses the Wilcoxon rank-sum test to explore changes in weight and height z-scores at baseline, total scores and subscores of ASQ-3, ABC, and SRS, and each item from 0 to 6 weeks and from 0 to 12 weeks. Linear mixed models were also used to analyze repeated measurements.

The present disclosure uses false discovery rate (FDR) to adjust the multiple comparison results. Secondary outcomes were analyzed using methods similar to those used for the primary outcomes. In addition, linear regression was performed to examine the correlation between clinical index and microbiome composition.

Microbiome Data Processing and Analysis:

Sequencing reads were filtered with QIIME2 (v2019.10) for quality control. Default parameters were denoised using Deblur, and abundance tables of samples were obtained by amplicon sequence variants (ASVs). Alpha diversity was calculated using QIIME2. Bray-Curtis distance was used to characterize β diversity of the microbiome. ASVs were assigned using a Sklearn-based classifier classification, wherein the classifier was trained on sequences with 99% similarity to Greengenes v13.8. It was confirmed by Kruskal-Wallis test that there were significant differences between the placebo and probiotic groups in the relative abundance of microbial phylum, genus, and alpha diversity. False discovery rate (FDR) based on Benjamini-Hochberg (BH) adjustment was used for multiple comparisons.

PICSRUSt2 was used to infer the functional content of microorganisms based on the abundance table of ASVs, and then to generate the Kyoto Encyclopedia of Genes and Genomes (KEGG) orthologs (KO), enzyme taxonomic numbers and pathway abundance tables. Differences in rates between the probiotic and placebo groups were analyzed using a permutation based nonparametric test, and the most significant difference features were plotted with Calour. All raw data from 16 s rRNA Illumina™ amplicon sequencing have been deposited in the National Center for Biotechnology Information (NCBI) Sequence Read Archive (SRA, PRJNA643297).

Results

1. Demographic Characteristics of PWS Subjects

Table 4 provides an overview of demographic characteristics and gastrointestinal (GI) symptoms of comorbidities in 65 participants, with no between-group differences observed (P>0.05). 47.5% of subjects in the study population showed one or more GI symptoms. The percentage of patients with GI symptoms was 37.4% lower in the probiotics group than in the placebo group, but the difference was not significant (P>0.05).

TABLE 4

| | | *Bifidobacterium animalis* subsp. *lactis* BL-11 group | Placebo group | P-value* |
|---|---|---|---|---|
| Age (month, N (mean ± SD)) | All the subjects | 31 (49.4 ± 34.3) | 34 (55.5 ± 41.9) | 0.26 |
| Gender (N (%)) | Male | 22 (67%) | 25 (71%) | 0.73 |
| | Female | 11 (33%) | 10 (29%) | |
| Genotype (N (%)) | Deletion | 11 (33%) | 9 (26%) | 0.71 |
| | Disome | 20 (61%) | 21 (60%) | |
| | Other/ unknown | 2 (6%) | 4 (11%) | 0.71 |

TABLE 4-continued

| | Bifidobacterium animalis subsp. lactis BL-11 group | Placebo group | P-value* |
|---|---|---|---|
| Weight (kg, mean ± SD) | 19.6 ± 13.7 | 23.7 ± 16.9 | 0.16 |
| Height (cm, mean ± SD) | 98.1 ± 18.8 | 104 ± 22.9 | 0.18 |
| BMI index (mean ± SD) | 18.4 ± 6.28 | 19.4 ± 6.01 | 0.22 |
| Gastrointestinal symptoms (≥1 item) | 0.87 ± 1.63 | 1.39 ± 1.75 | 0.24 |

No serious adverse events were observed. For all observed adverse events and primary reasons for dropout, there were no significant differences between the two groups (P>0.05).

2. Effects of Probiotics on Weight, Height, Psychometric Measurement, and CGI-I

Figure 9:
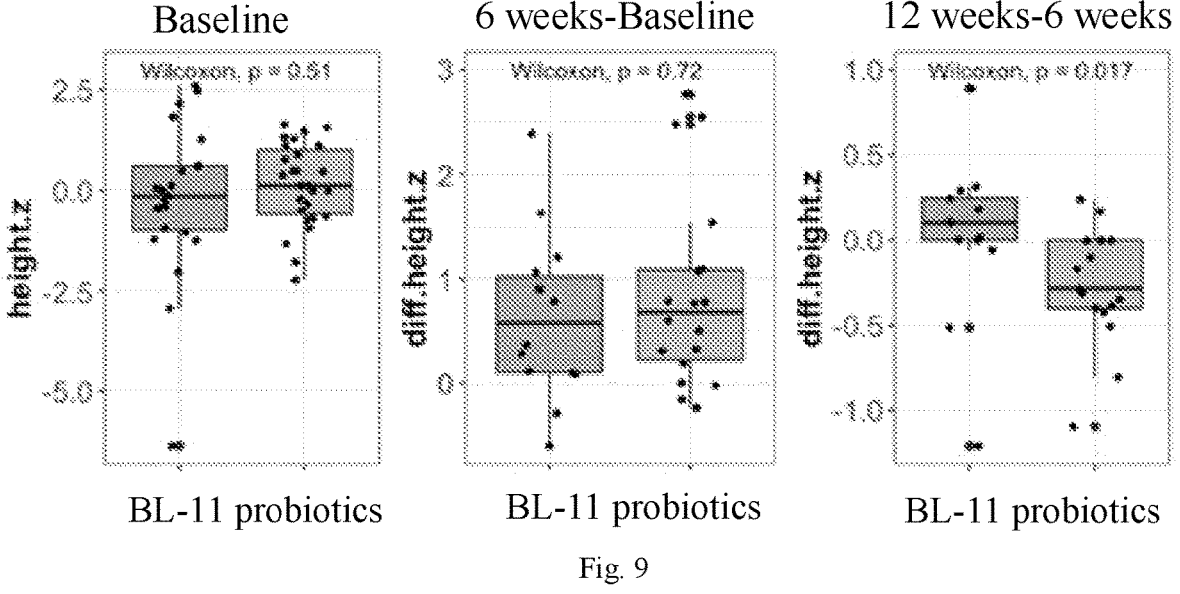
FIG. 9 shows changes in human height before the administration of probiotics or placebo and from 0 to 12 weeks after the administration of probiotics or placebo.
Figure 10:
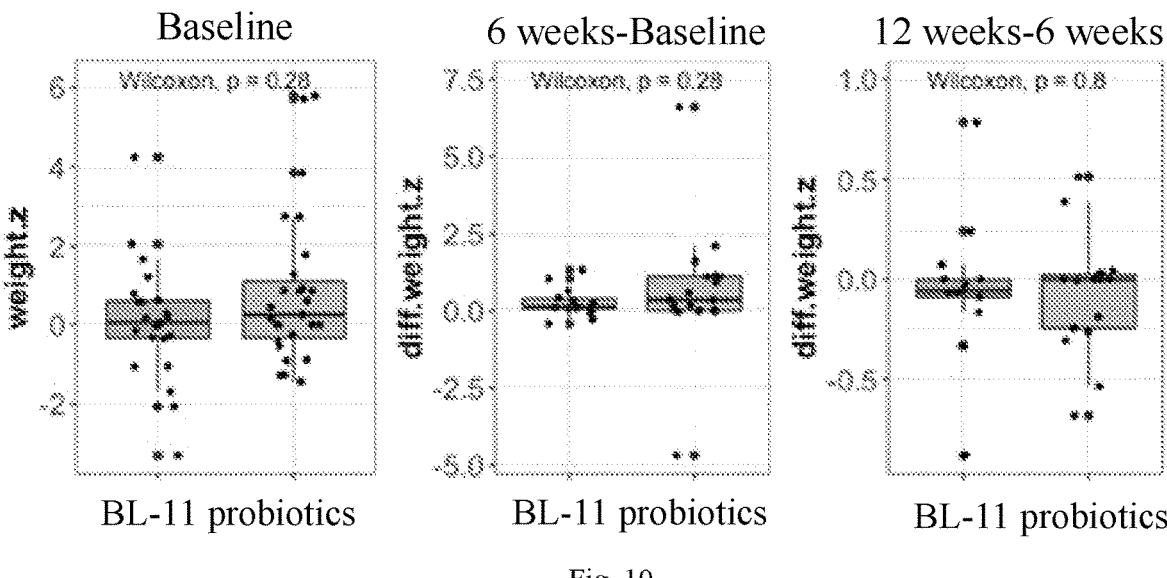
FIG. 10 shows changes in body weight before the administration of probiotics or placebo and from 0 to 12 weeks after the administration of probiotics or placebo.
Figure 11:
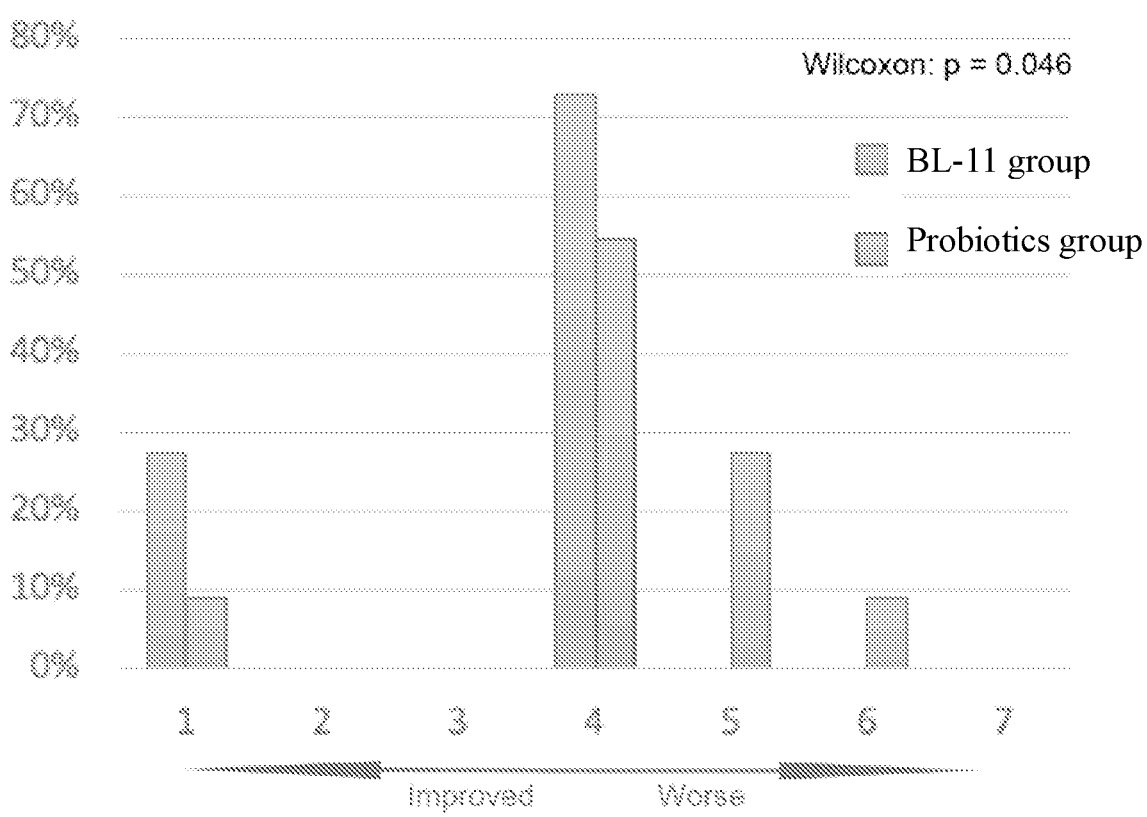
FIG. 11 shows an improvement in symptoms after the administration of probiotics or placebo.

Anthropometric data were collected and analyzed throughout treatment. The height of the probiotics group was significantly higher than that of the placebo group from 6 to 12 weeks (probiotics group had an average increase of 2.58 cm, which was significantly higher than the placebo group, P<0.05, FIG. 9). The probiotics group had a greater weight loss over time than the placebo group, but the between-group difference was not significant (FIG. 10). Linear mixed-effects model analysis showed the probiotics group had a trend toward greater improvement than the placebo group in psychometric scores (including ASQ-3, ABC, SRS, and RRB), but the differences were not significant (P>0.05). Global improvement in symptoms during the treatment, measured using the CGI-1 scale, was greater in the probiotics group than in the placebo group (FIG. 11, P<0.05).

3. Changes in Microbiome Composition and Function Under Probiotic Intervention

Figure 12:
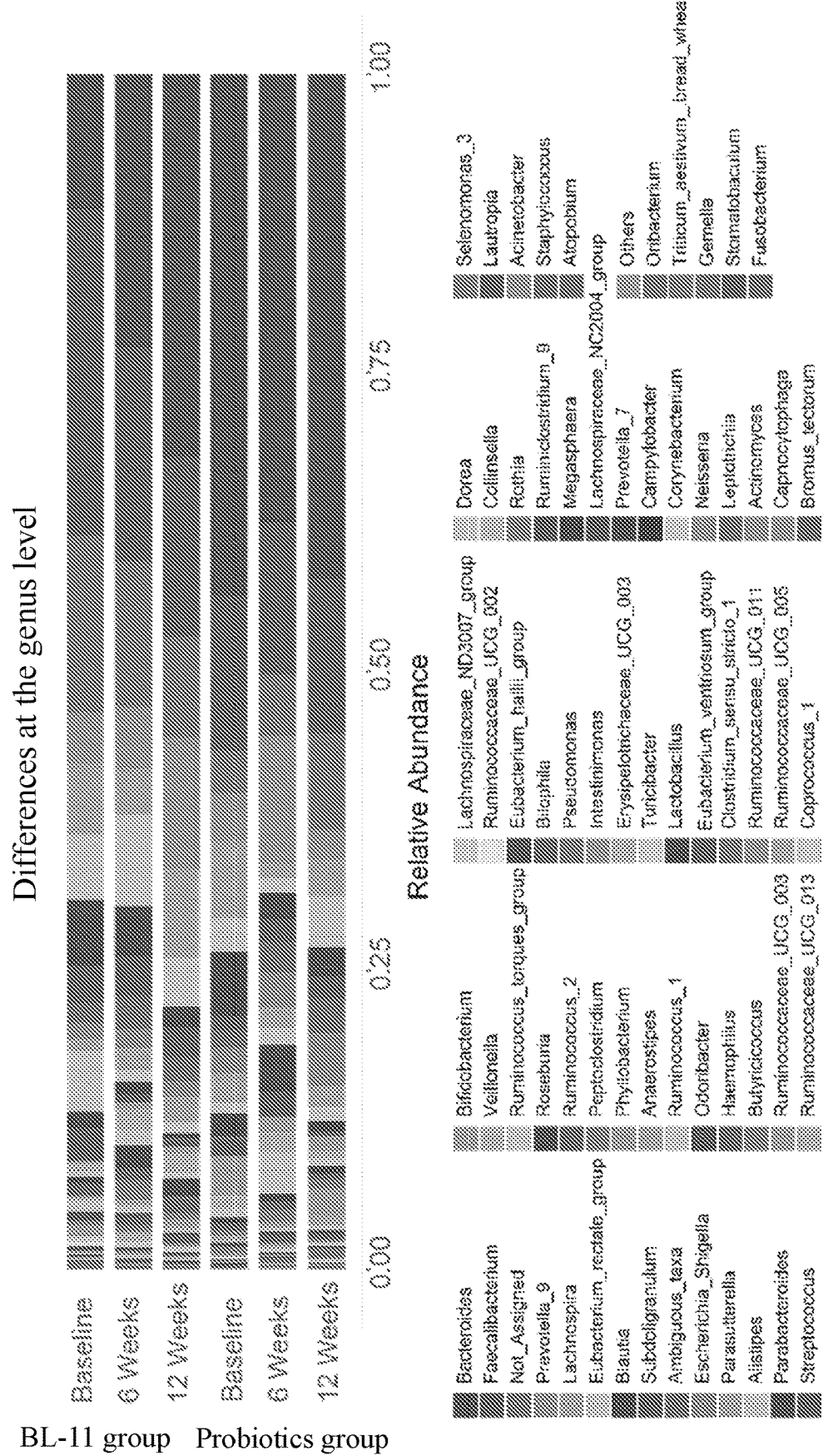
FIG. 12 shows a composition of intestinal microbiota at the genus level after the administration of probiotics or placebo.

After sequencing, the intestinal microbiome composition of PWS individuals was differentially enriched in two groups during the intervention. The overall relative abundance levels of specific bacteria are shown in FIG. 12. After 6 weeks, there was a slight increase in α diversity in the probiotic group compared with the placebo group, and the difference was not significant. β diversity analyzed by permutable multivariate analysis of variance (PERMANOVA) showed that separation of the two groups could be achieved by probiotic treatment (F-statistic=2.2526, $R^2$=0.035613, P<0.05, NMDS pressure=0.19048, FIG. 13).

Figures 13, 14:
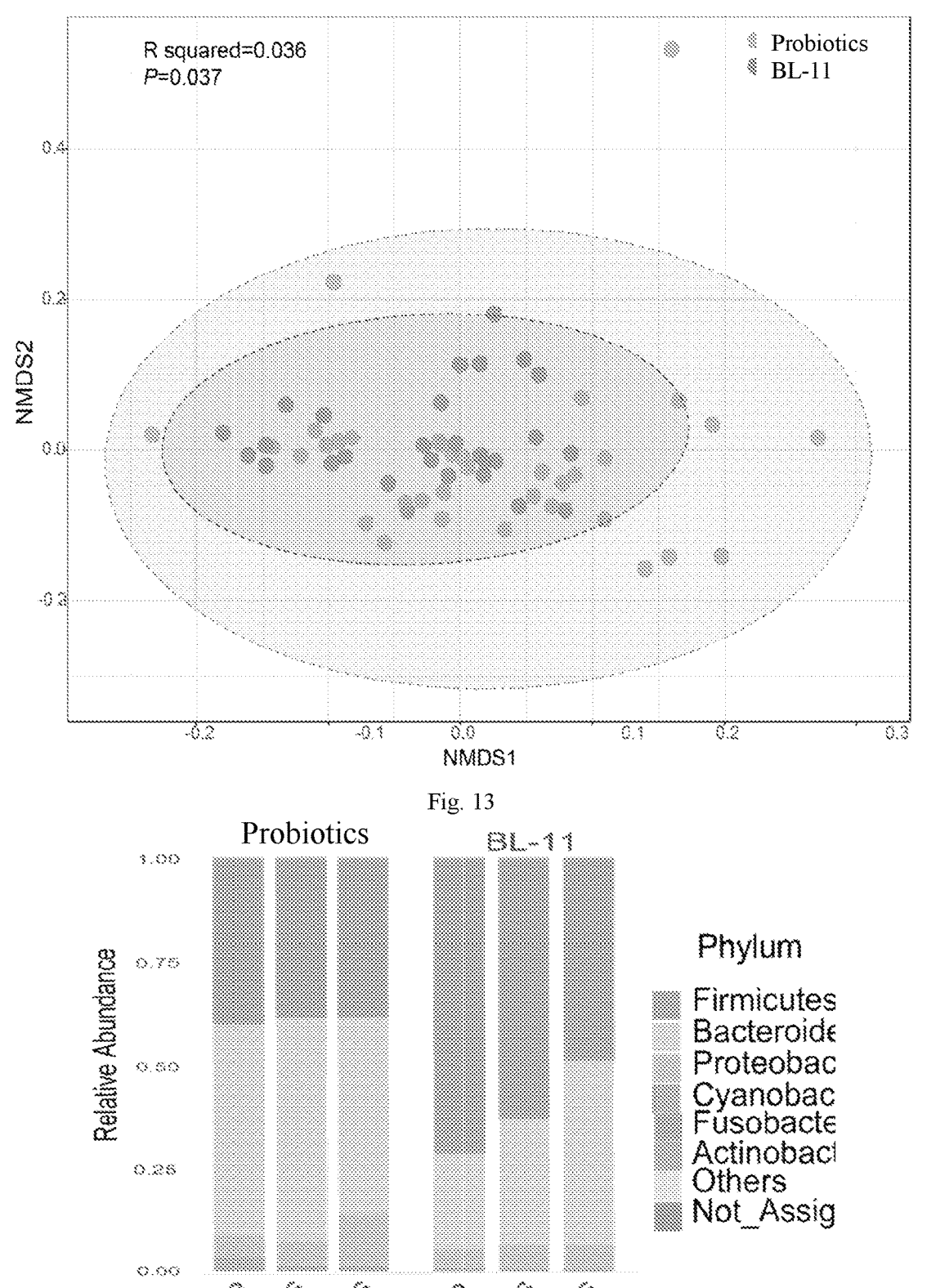
FIG. 13 shows a comparison of intestinal microbiota at the level of metabolic pathways before and after the administration of probiotics or placebo.
FIG. 14 shows a composition of intestinal microbiota at the phylum level after the administration of probiotics or placebo.
Figure 15:
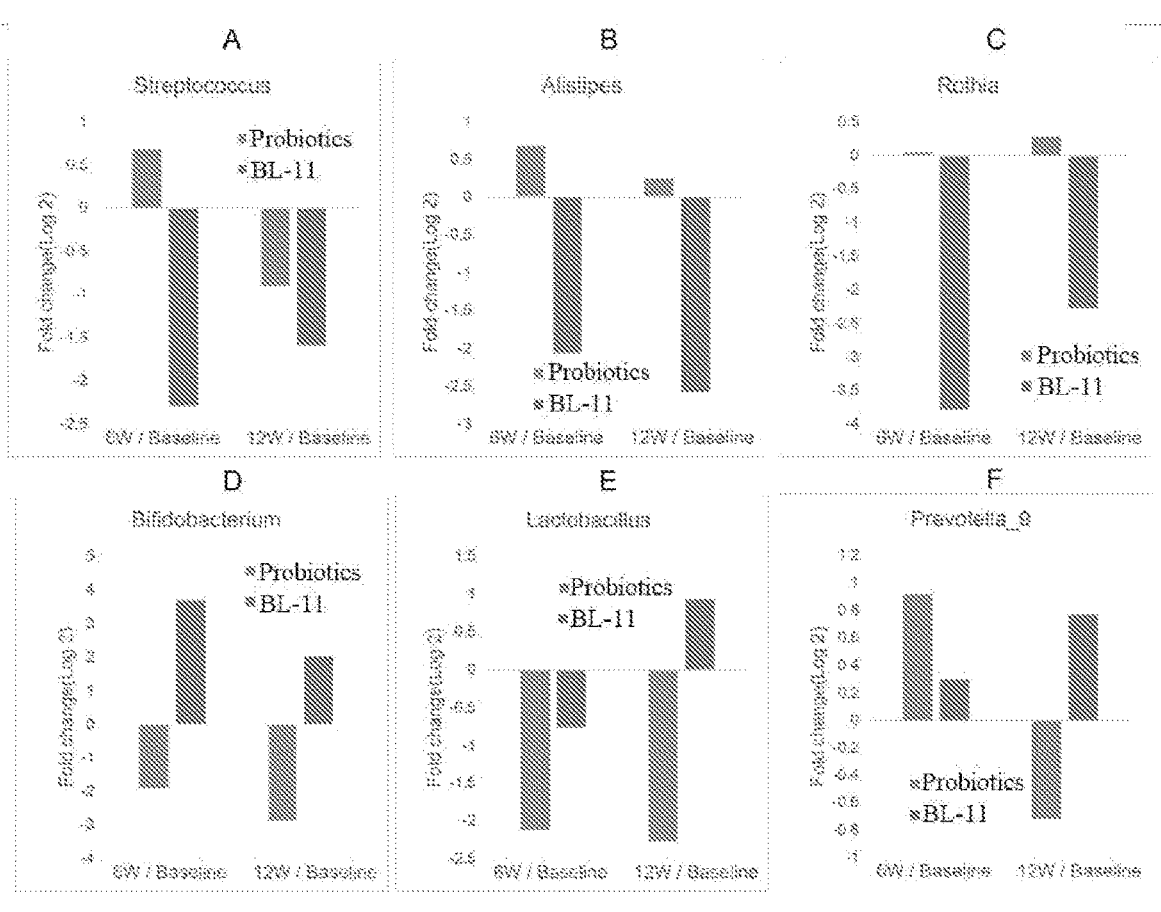
FIG. 15 shows a comparison of intestinal microbiota in representative strain composition before and after the administration of probiotics or placebo.

In order to characterize changes in the abundance of bacteria that may be clinically significant during the intervention, the present disclosure presented fold changes for genera and families of several selected bacteria, as shown in FIG. 14. In the probiotics group, at weeks 6 and 12, the relative abundance of Lachnospiraceae ND3007, Ruminococcaceae UCG-003, Streptococcus mutans, Comamonadaceae, Alistipes and Rothia was reduced compared with baseline. In the probiotic group, beneficial bacterial genera such as Bifidobacterium, Lactobacillus, and Prevotella 9 increased significantly at 12 weeks compared with baseline (FIG. 15).

Figure 16:
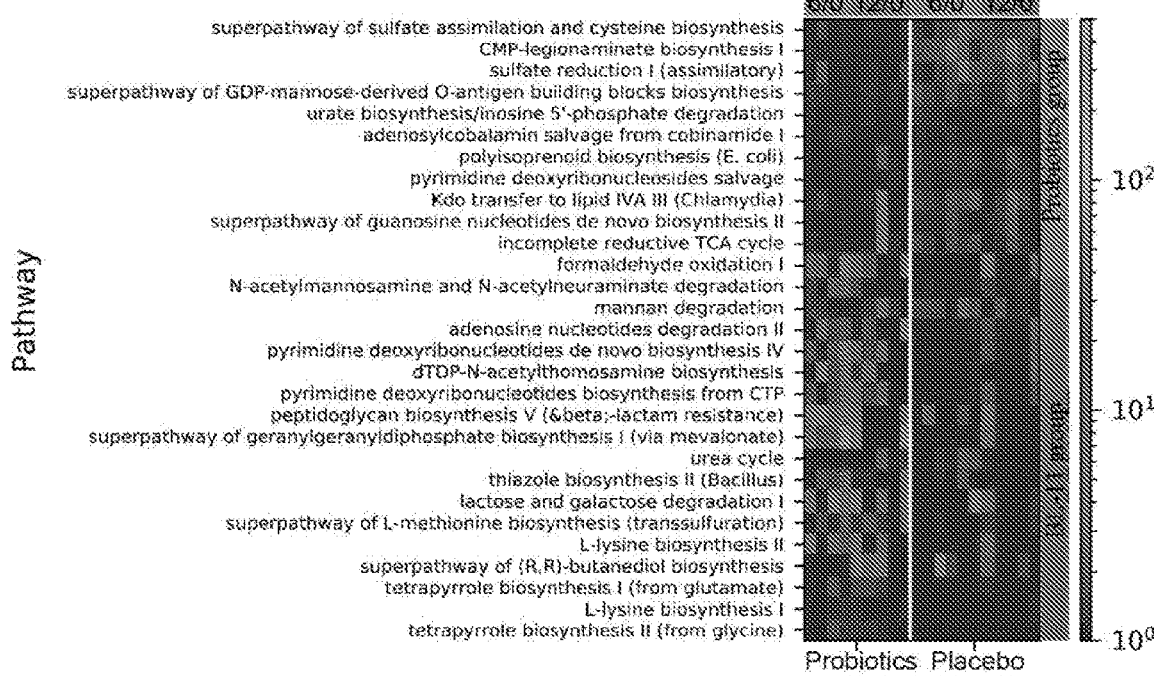
FIG. 16 shows a comparison of intestinal microbiota at the functional gene level before and after the administration of probiotics or placebo.
Figure 17:
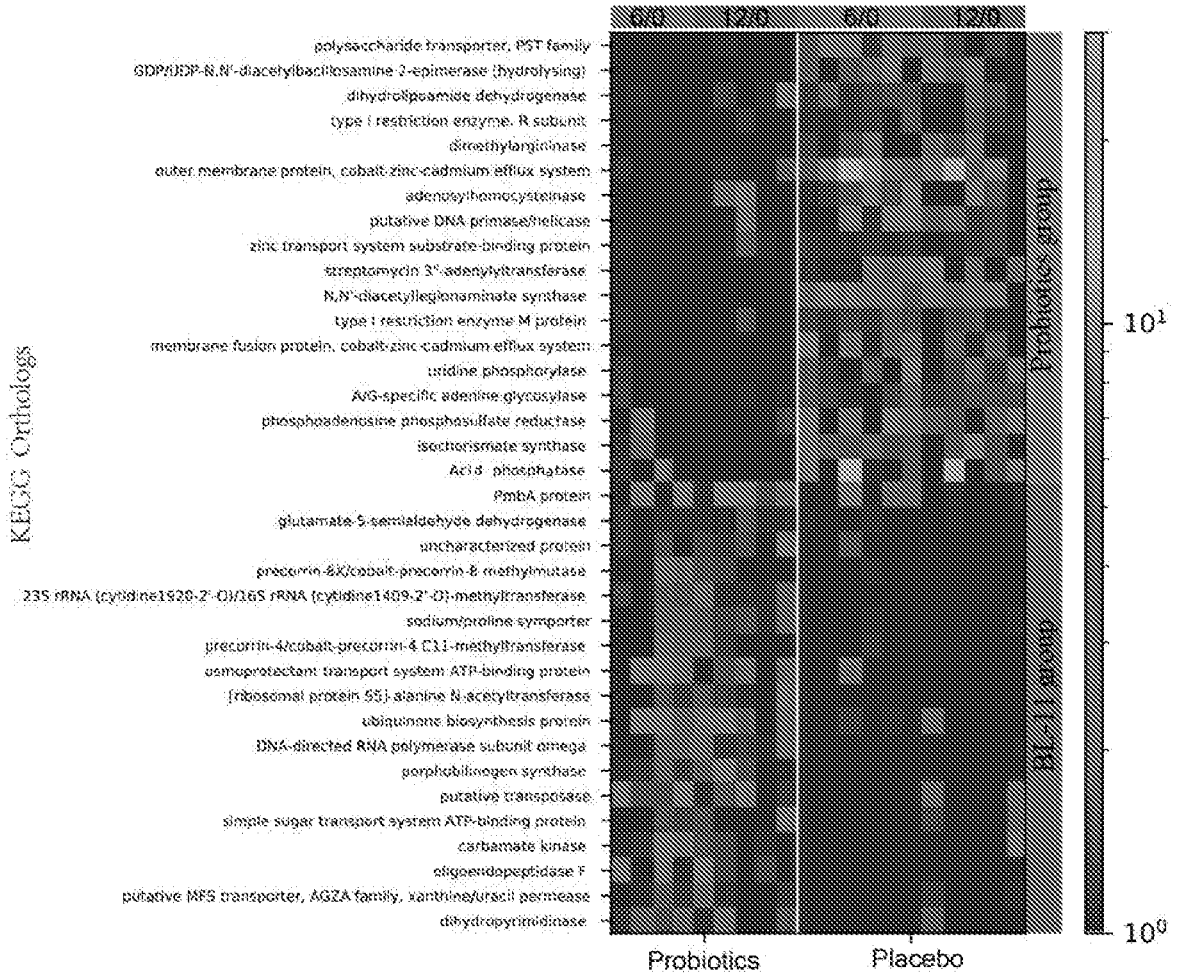
FIG. 17 shows a comparison of intestinal microbiota at KO level before and after the administration of probiotics or placebo.
Figure 18:
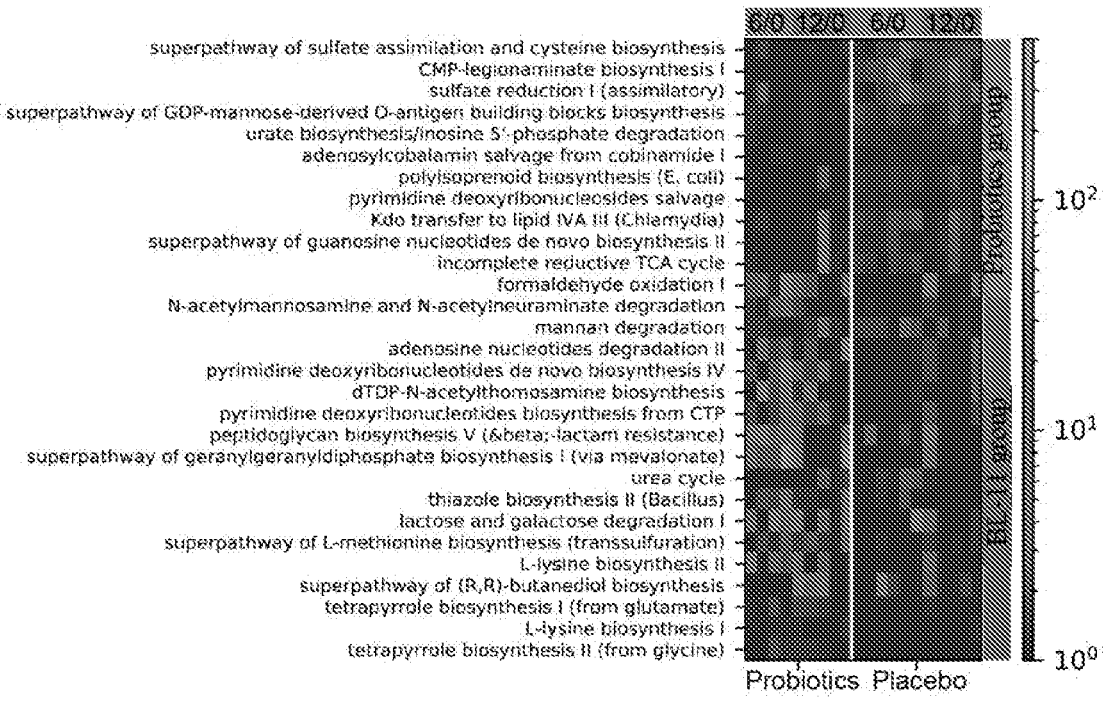
FIG. 18 shows a comparison of intestinal microbiota at the level of metabolic pathways before and after the administration of probiotics or placebo.
Figure 19:
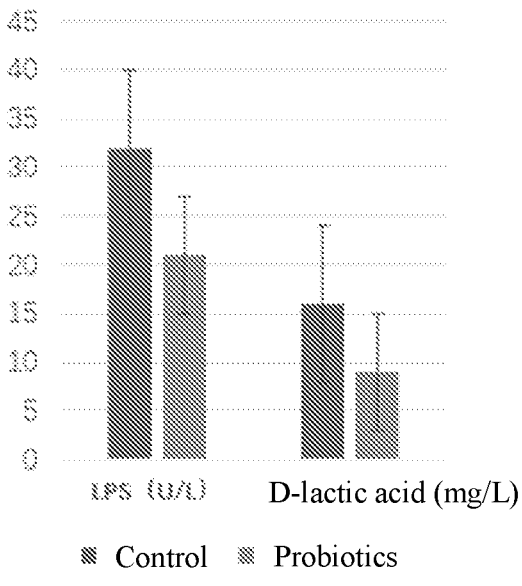
FIG. 19 shows results of the intestinal permeability measurement.
Figure 20:
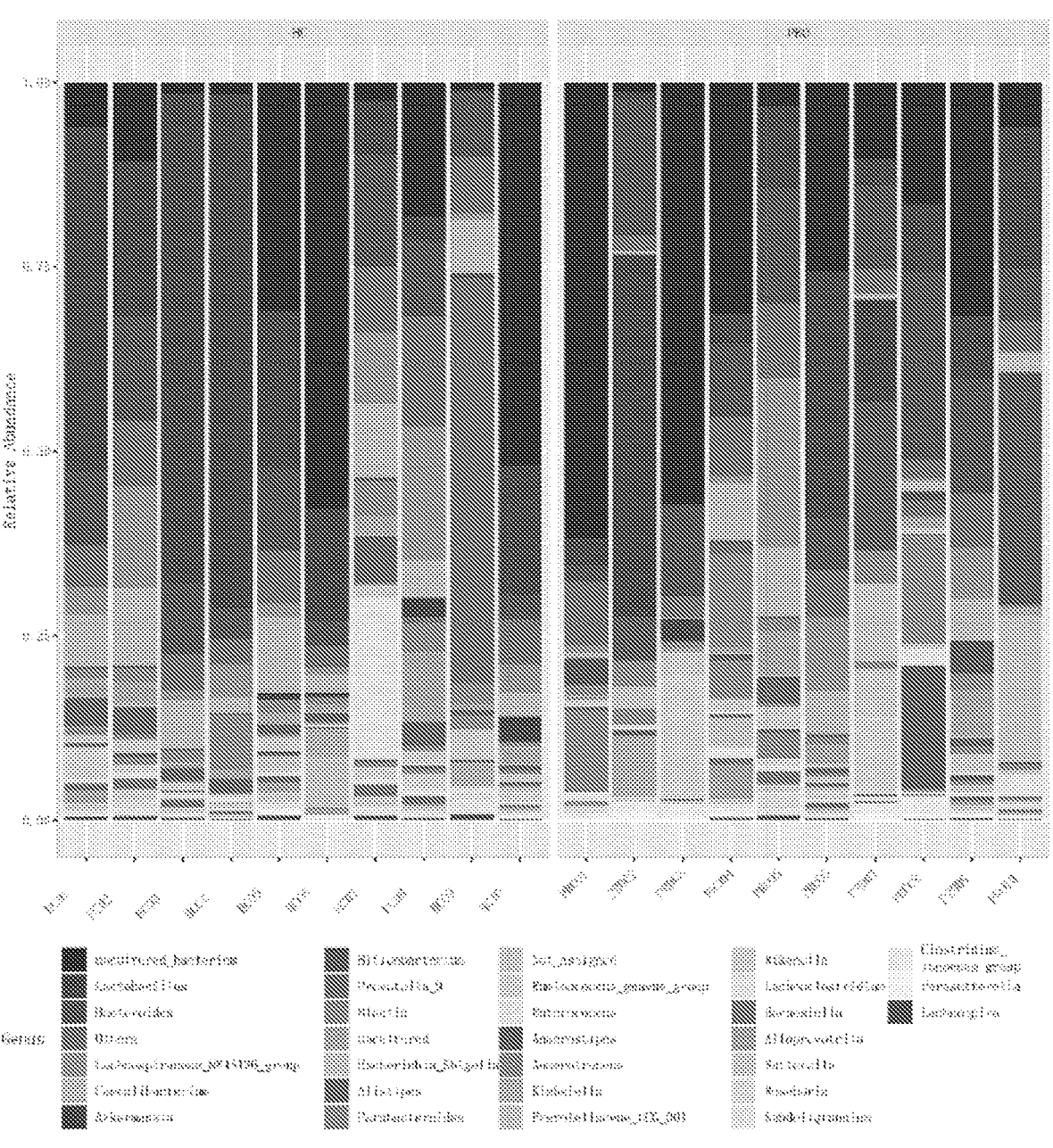
FIG. 20 shows a composition of intestinal microbiota in each group at the genus level.
Figure 21:
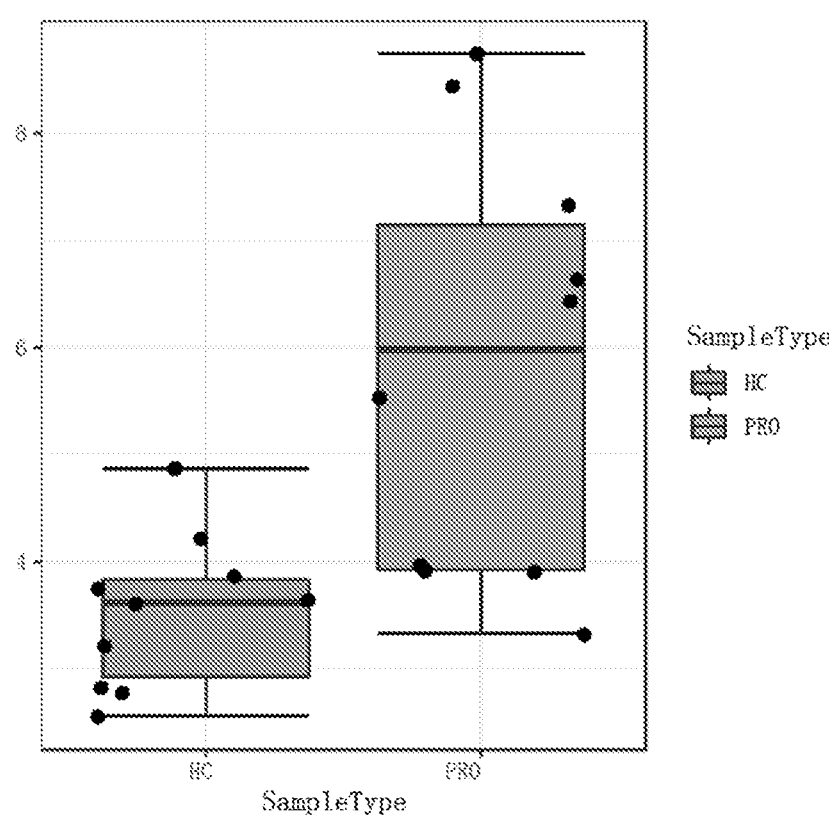
FIG. 21 shows a difference in *Bifidobacterium* genus between the two groups.
Figure 22:
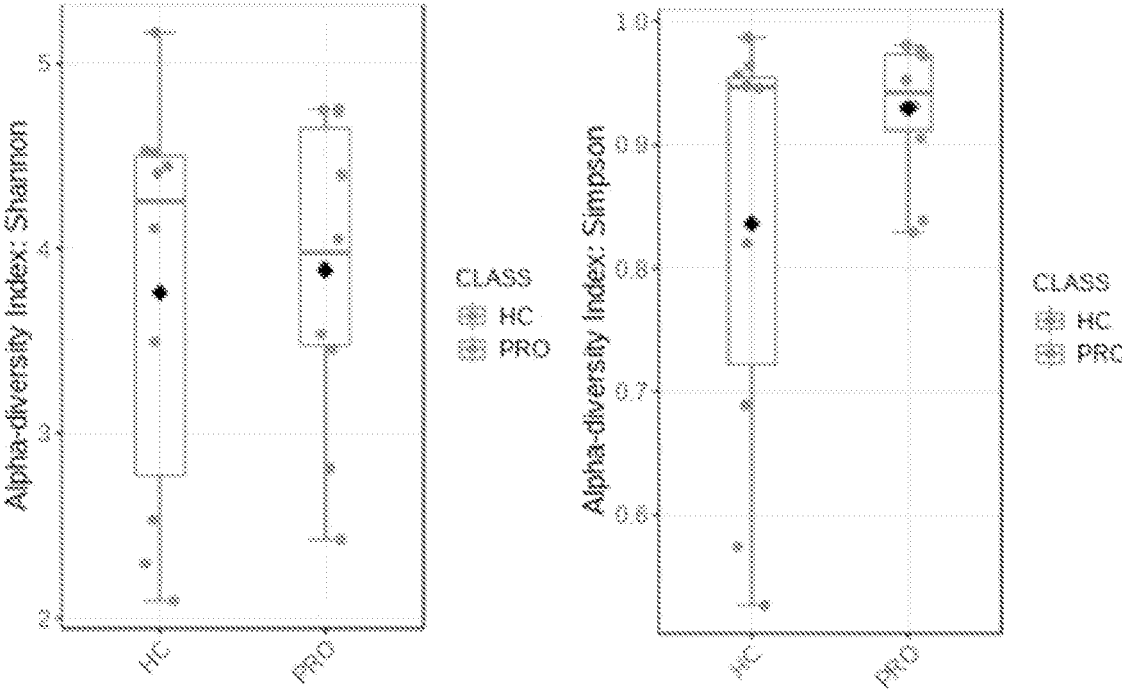
FIG. 22 shows results of a diversity index.
Figure 23:
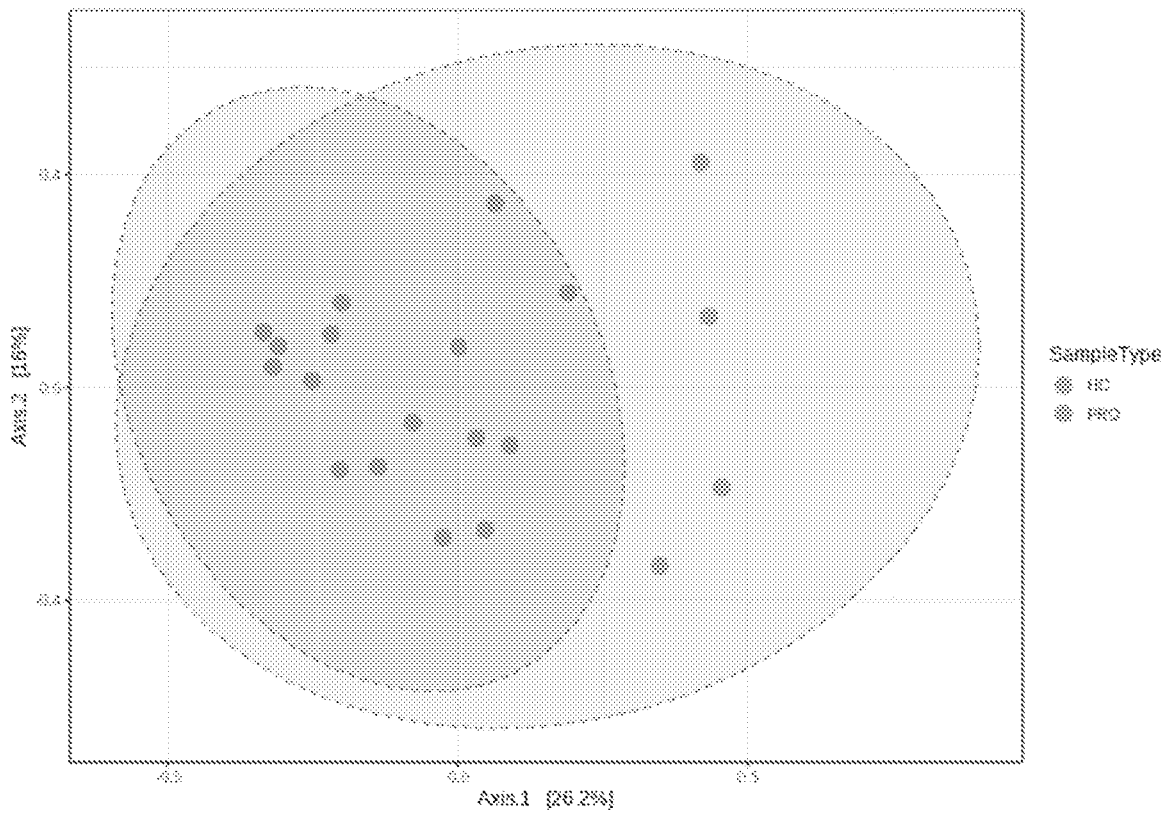
FIG. 23 shows PCoA analysis results of the β diversity index analysis.

Functional gene prediction analysis indicated that several genes in the probiotic group had different abundances after the 12-week treatment. All of genes encoding ubiquinone biosynthesis protein (ubiB, k03688), desaturase (EC: 1.3.99.29), desaturase (lycopene formation) (EC: 1.3.99.31), and all-trans-ξ-carotene desaturase (EC: 1.3.99.26) were up-regulated, while genes encoding dimethylargininase (k01482) and acid phosphatase (phoN, k09474, EC: 3.1.3.2) were down-regulated (FIG. 16). These findings did not meet false discovery criteria for significance of multiple comparisons. The results of the analysis of the predicted KEGG pathways and the predicted KO shown in FIGS. 17 and 18 further show the comparison of the gene expression between the probiotic and placebo groups.

4. Correlation Between Intestinal Microbiota Abundance and Clinical Index

Clinical index were correlated with the abundance of bacterial genera. Two correlations were found in the probiotic group, and no correlation was found in the placebo group. At week 6, there was a positive correlation between RRB score and Rothia in the probiotics group (R=0.97, p<0.005).

In a 12-week randomized, double-blind, and placebo-controlled experiment involving 65 PWS patients of the present disclosure, subjects treated with Bifidobacterium animalis subsp. lactis BL-11 showed a significant increase in height and a slight change in weight. The present disclosure provides new evidence for Bifidobacterium animalis subsp. lactis BL-11 as an early intervention for PWS patients. Moreover, the present disclosure finds that there is a significant difference in f diversity of intestinal microbiome between the probiotic group and the placebo group after treatment, and that baseline f diversity is directly related to long-term weight loss when adhering to the controlled diet. Therefore, supplementation with Bifidobacterium animalis subsp. lactis BL-11 may improve intestinal microbiota composition and prevent obesity or promote diet-induced weight loss. Supplementation with Bifidobacterium animalis subsp. lactis BL-11 may also improve the infant and youth physical development.

In addition, the present disclosure found that the overall symptoms were significantly improved in the probiotic group and the placebo group after treatment, and the psychometric indexes were improved. Therefore, supplementation with Bifidobacterium animalis subsp. lactis BL-11 may have a role in improving the infant and youth mental development, behavior, or emotional state.

Example 5

This example is used to illustrate the preparation of BL-11 lyophilized bacterial powder.

The storage solution of BL-11 bacteria was resuscitated in a water bath at 37° C. until all the liquid in the frozen storage tube melted. The MRS Medium was streaked in sections, and the bacteria were cultured anaerobically at 37° C. for 12-24 hours. Single colonies were selected and inoculated into anaerobic culture tubes containing liquid medium, sealed, and incubated at 37° C. for 6-12 hours. When the OD600 value of bacterial solution stopped growing, the fermentation was stopped. The bacterial solution was fermented and incubated at a constant temperature of 40° C. for 6-12 hours with stirring. The constant pH of the bacterial solution was maintained at 5.4±0.5. When the OD600 value of the bacterial solution stopped increasing, the fermentation was stopped immediately. The sludge was collected by centrifugation, and the lyophilized protective agent was added at a volume ratio of the sludge:lyophilized protective agent=1:1-10. After stirring and mixing, the powder was lyophilized using a freeze dryer. The lyophilized powder was collected, crushed and packaged according to quality requirements.

Example 6

This example is used to illustrate BL-11 lyophilized bacterial powder for use in the production of food.

The lyophilized bacterial powder produced from *Bifidobacterium animalis* subsp. *lactis* BL-11 provided in the present invention can be used in ordinary food or health food such as yogurt, fermented milk, cheese. Preferably, in the food, the dose of *Bifidobacterium animalis* subsp. *lactis* BL-11 for preparing yogurt is $1.0 \times 10^6$-$1.0 \times 10^8$ CFU/kg, more preferably $1.2 \times 10^7$-$1.5 \times 10^8$ CFU/kg. The preparation method is a direct addition method or a post addition method. When using the direct addition method, the lyophilized bacterial powder is used as fermentation strain, and added in proportion after raw milk was sterilized and reduced to the appropriate temperature, and fermentation was then carried out at 40-43° C. for 10-48 hours to obtain a product of fermentation. After stirring and mixing, the product of fermentation is divided into cups or bags as a finished product. When using post addition method, the lyophilized bacterial powder is added in a certain proportion after the fermentation of yoghurt, and then stirring, mixing and divided into cups or bags as a finished product.

Example 7

This example is used to illustrate BL-11 lyophilized bacterial powder for use in the production of dietary nutritional supplements, and probiotics.

The lyophilized bacterial powder produced from *Bifidobacterium animalis* subsp. *lactis* BL-11 provided by the present invention can be used for the production of probiotics. Probiotics lyophilized powder comprises 0.5-30 parts of BL-11 lyophilized bacterial powder, 5-20 parts of bacteria such as *Lactobacillus fermentium, Lactobacillus helveticus, Lactobacillus reusei, Lactobacillus plantarum, bifidobacterium adolescentis, Bifidobacterium breve,* and *Bifidobacterium* longum, 20-70 parts of prebiotics such as galactooligosaccharide, fructooligosaccharide, and inulin, 5-10 parts of nutrients such as GABA, tryptophan, lycopene, 0-carotene, vitamin B6, vitamin B12, coenzyme Q10, taurine, pectin, 0-glucan, fucose, carrageenan, guar gum, and dietary fiber, and further comprises 0.1-5 parts of antioxidants/anti-inflammatory substances, such as tocopherol, carotenoids, ascorbic acid/vitamin C, ascorbic acid palmitate, polyphenols, glutathione and superoxide dismutase. The probiotics is added at a total viable count of $2.0 \times 10^6$-$2.0 \times 10^{10}$ CFU/g, preferably $3 \times 10^7$-$3 \times 10^{10}$ CFU/g. Each of the other bacteria is added at a dose of $1 \times 10^6$-$3 \times 10^9$ CFU/g. The preparation process includes: weighting raw materials in proportion, mixing, packing and quality inspection, etc.

Example 8

This example is used to illustrate the effects of BL-11 lyophilized bacterial powder on improving intestinal permeability and behavior.

Gut microbiota and gut-brain axis (GBA) play a two-way communication effect in the regulation of stress response. Microbiota communicates with the gut-brain axis through different mechanisms. It interacts directly with mucosal cells, influences brain development and behavior through immune cells, and through contacting with nerve endings. Stress in the brain can also have an effect via GBA on the gut microbiome, which is responsible for GI dysfunction and dysregulation. Stress responses also affect the synthesis of microbial by-products and precursors that enter the brain through the blood and hindbrain regions, release cytokines through mucosal immune cells, release gut hormones such as serotonin (5-HT) through enteroendocrine cells, or through afferent nervous pathway, including the enteric nervous system.

Preparation of probiotics preparation: the probiotic preparation comprises lyophilized powder containing BL-11, β-carotene, vitamin B6, vitamin B12, coenzyme Q10 and maltodextrin, and the control group was maltodextrin. The experimental mice were treated with 10 billion CFU/mouse/day by gavage.

Twenty C57BL/6J mice aged 6 weeks old were housed in four cages with five mice per cage, and fed and watered adlibitum. Food and water intake were recorded twice weekly. The mice were divided into control group and probiotics group, with 10 mice in each group. After one week of acclimatization, the mice were randomly divided into two groups: model group and probiotics intervention group. The growth conditions of the experimental mice were: ambient temperature (23±2°) C, relative humidity (50±10) %, and light mode (12 h dark/12 h light).

The model of chronic stress caused by physical stimulation was adopted. The specific stimulation methods included: (1) fasting and water deprivation for 24 hours; (2) continuous light for 24 hours; (3) clamping tail with an iron clip from 1 cm of the tail tip for 3 min/time; (4) restraint stress with circular sleeve restraint for 2 h/day. One or two different stress stimulation were used every day, and the stimulation time was not fixed for 4 weeks.

From the sixth week, the stress stimulation was stopped, and the sucrose preference test, step-down test and open field test were carried out. After the behavioral test, the physical and chemical indexes of mice in each group were measured. SPSS statistical software was used to process the data, which was expressed as mean±standard deviation. Independent sample test was used for comparison between groups, $P<0.05$ was considered statistically significant.

1) Sucrose Preference Test

Before the experiment, two identical water bottles, one containing pure water and the other containing aqueous solution of 1% sucrose, were placed on the cage frame at the same time, and the experimental mice were allowed to acclimate to the aqueous solution of sucrose for 24 hours. In order to avoid the interference caused by the drinking habits of the experimental mice, the position of the water bottle was changed every 1 hour. After acclimation, the mice were fasted and water deprived for 24 hours. One bottle of pure water and one bottle of aqueous solution of 1% sucrose were placed on each cage before the experiment, and the consumptions of aqueous solution of sucrose and pure water was recorded every 3 hours.

Sucrose preference = consumption of aqueous solution of sucrose/

(consumption of aqueous solution of sucrose + consumptions of pure water) × 100%.

The results showed that the control group had a decreased preference for the aqueous solution of sucrose (49.63%±15.79), while after supplementation of probiotics, the preference for the aqueous solution of sucrose was increased (68.79%±12.34), indicating that probiotics could improve the anhedonia caused by stress stimulation.

2) Step-Down Test

Step-down instrument test box (DTT-2 mouse step-down, Institute of Materia *Medica*, Chinese Academy of Medical Sciences) was used. The test box is about 120 cm long, 12 cm wide and 30 cm high, and is made of plexiglass. There were six chambers, each 12 cm long, 12 cm wide, and 30 cm high. The test box allowed six mice to be tested at same time. The bottom of the test box is covered with a copper gate, which is connected to the power supply through a wire, and the current voltage is set to 36V. An insulation table (a pentagon-shaped wooden block with a long diameter of 5.7 cm, a short diameter of 4.5 cm and a high of 4.8 cm) was placed on the copper gate in the test box as a safety area for animals to avoid electric shocks. The test box was connected to a computer automatic recording system. In the experiment, the mice were put into the step-down instrument test box to acclimate for 5 minutes, and then gently placed on the table. The copper gate was electrified. When the mice jumped off the table and touched the copper gate, they would receive electric shocks. The normal avoidance response was to jump on the table and return to the safety zone to escape the electric shock. This learning was carried out for 5 minutes, and the number of electric shocks (the number of errors) within 5 minutes was recorded, which was regarded as the learning score. After 24 hours, memory tests were performed. The mice were placed on the table, and the time from staying on the table to receiving the first electric shock as the latency period, and the number of errors within 5 minutes (the number of electric shocks that all limbs of the mice touched the copper gate at the same time) were recorded as the evaluation indexes of memory function.

Compared with the normal control group, the probiotics group has a significantly shortened latency period in the step-down test (P<0.05). There was no significant difference in the number of errors in step-down test between the two groups, but the probiotics group showed a decreasing trend in the number of errors. The results showed that the probiotics could improve the memory function of one-time avoidance response in mice (see Table 5).

TABLE 5

| Effect of probiotics on memory function of avoidance response | | |
|---|---|---|
| | Number of errors (times) | Latency period (S) |
| Control group | 1.45 ± 0.82 | 268.32 ± 50.63 |
| Probiotics group | 1.07 ± 0.87 | 248.05 ± 82.33 |
| P value | 0.0348 | 0.0782 |

3) Open Field Test

The open field test analysis system is used to observe and study the neuropsychological changes of animals, and various behaviors of animal. For example, animals are afraid of the new open environment, after entering the open environment, in which animals mainly act in the peripheral area and less in the central area. However, the exploratory characteristics of animals promote their motivation to act in the central area, and the resulting anxiety can also be observed. It was used to assess the level of voluntary active activity and anxiety in animals.

The mice were moved to the open field test room 60 min before the experiment to acclimate to the environment in advance. In the experiment, the mice were removed from the cage and placed in the open field test device in the behavioral experimental station (the box has length×width×height of 100 cm×100 cm×40 cm, blue inner and bottom sides, and the camera placed directly above the central area). At the beginning of the experiment, the mice were placed in a fixed position in the central area, with the head fixed to one side each time, and the light mask curtain was quickly pulled. After recording the number, date and status of the mice in the operating software, the recording system was turned on, the nine-square mode was selected with ratio of central area of 0.5, and the camera above the open field device and the connected monitor were opened. Each mouse was measured for 5 minutes, and the activity of the mouse was recorded. The measurements included movement time, total distance, percentage of time spent in the central area (time spent in the central area LPMM=s), percentage of horizontal movement in the central area (distance of horizontal movement in the central area and L distance of horizontal movement), percentage of horizontal movement in the four sides area (distance of horizontal movement in the four sides area and L distance of horizontal movement) and percentage of horizontal movement in the four corners area (distance of horizontal movement in the four corners area and L distance of horizontal movement). The times of standing and grooming were recorded, and then the environment in the box was cleaned with 75% alcohol. After the alcohol volatilized and became odorless, the next mouse was measured. The results are shown in Table 6.

Compared with the control group, the number of entry into the central area and the time spent in the central area of the probiotic group were significantly higher (P<0.05). The numbers of standing and grooming increased significantly (P<0.05), while there was no significant difference in the total movement distance. There was no significant difference in results of other open field behavior.

TABLE 6

| Results of open field behavior experiments in mice | | | | |
|---|---|---|---|---|
| | Total movement distance (cm) | Time spent in the central area (S) | Number of entry into the central area | Number of standing | Number of grooming |
| Control group | 383.34 ± 189.82 | 6.45 ± 2.14 | 3.22 ± 2.56 | 9.32 ± 6.78 | 4.88 ± 1.68 |
| Probiotic group | 486.74 ± 212.71 | 9.87 ± 2.77 | 5.84 ± 2.97 | 13.87 ± 5.94 | 6.29 ± 2.13 |

4) Measurement of Intestinal Permeability

To assess intestinal permeability in vivo, serum D-lactate, LPS content was measured.

D-lactic acid is a metabolite of bacterial fermentation, and can be produced by a variety of intestinal bacteria. Even if D-lactate is ingested from food, it is rarely absorbed into the blood under normal conditions. Mammals do not possess an enzymatic system for the rapid degradation of D-lactate. Therefore, when intestinal mucosal permeability is increased, a large amount of D-lactic acid produced by bacteria in the gut passes through the damaged mucosa into the blood, increasing the level of D-lactic acid in the blood.

Lactic acid has D-form and L-form. The normal human body only has L-lactate, and bacteria and other microorganisms can produce D-lactic acid. The level of D-lactic acid in blood can timely reflect the degree of intestinal mucosal damage and changes in permeability. It can be used for the auxiliary evaluation of intestinal infection, endotoxemia, systemic inflammatory reaction, recurrent fever, vomiting, etc.

Lipopolysaccharide (LPS), also known as bacterial endotoxin, is a component of the cell wall of Gram-negative bacteria. LPS is a toxic substance for animals. The structure of LPS is consisted of three parts: glycolipid domain-lipid A, sugar residue short chain-core oligosaccharide, and hypervariable polysaccharide domain-O antigen. The structure of LPS determines its agonist/antagonist effect on TLR4. In vivo, LPS binds to TLR4/MD-2 receptor complex and activates different signaling pathways through myd88-dependent or TRIF-dependent pathways. The expression of TLR in different parts of intestinal epithelial cells is different, preventing the inflammatory response caused by LPS and fighting against pathogenic bacteria.

Bacterial translocation is the process by which live intestinal bacteria enter the body from the gut through the epithelial mucosa. Bacteria can enter the lymphatic system through the mesenteric lymph nodes and circulate systemically. They can also enter the circulation, causing bacteremia, and can locate in tissues. Bacterial translocation can result in small intestinal bacterial overgrowth, intestinal injury, and shock. Any stress response including psychological and physiological tress response that leads to intestinal permeability, could potentially lead to bacterial translocation.

LPS is associated with the pathogenesis of many diseases, such as IBD and enterocolitis and other intestinal diseases, and even Parkinson's and Alzheimer's diseases. LPS can not only enter the blood, but also enter and remain in the brain for a lifetime, which may cause Alzheimer's disease.

The level of LPS in the blood can reflect the permeability of the intestine, and the normal intestinal barrier does not allow LPS to enter. The higher level of LPS in the blood indicates the translocation of intestinal bacteria or LPS into the blood, indicating the increase of intestinal permeability and the increase of intestinal leakage symptoms. The amount of LPS in the blood can also indicate the inflammatory response and stress state. Excessive LPS can cause abnormal immune system, chronic or acute inflammatory response, and acute inflammation such as fever and pain. It can be used for the auxiliary evaluation of intestinal infection, endotoxemia, systemic inflammatory reaction, recurrent fever, vomiting, mental illness, stress response, etc.

At the end of the experiment, blood was collected from tail vein terminals. The blood was centrifuged at 3000 g for 15 minutes. The intestinal barrier function analysis system (JY-DLT, Beijing Zhongsheng Jinyu diagnostic technology Limited by Share Ltd) was used to detect the content of D-lactic acid and LPS in serum according to the operating instructions.

The results showed that compared with the control group, the levels of LPS and D-lactic acid were significantly decreased in the probiotics group (P<0.05). The results indicate that stress stimulation leads to an increase in intestinal permeability, and probiotics can reduce intestinal permeability and reduce the risk of endotoxemia and systemic inflammatory response.

Example 9

This example is used to illustrate the effect of BL-11 lyophilized bacterial powder on the intestinal microbial composition.

After the above behavioral experiments, the collected cecal contents were stored at −80° C. Feces were collected from the mice in the two groups, and the DNA of fecal microbiota was extracted by TIANmap fecal DNA kit (TIANGEN™, catalog number DP328). The extracted DNA was quantified using a Qubit instrument. Detection was performed using 1% agarose gel electrophoresis: voltage 100V for 40 min. UVI gel imaging system is used to take pictures for recording. There were no stray bands and tailing in DNA electrophoresis, indicating that the DNA fragment was pure and was not significantly degraded. An appropriate amount of sample was taken and placed into a centrifuge tube and dilute to 1 ng/μL with sterile water. DNA was stored in a refrigerator at −20° C. for use.

Amplification of bacterial 16S rRNA gene: Diluted genomic DNA was used as a template, and specific primers with Barcode were used depending on the region selected for sequencing. Bacterial universal primers 341F (CCTAYGGGRBGCASCAG, SEQ ID NO. 3) and 806R (GGACTACNNGGGTATCTAAT, SEQ ID NO. 4) were used to amplify the V3-V4 region of the bacterial 16S rRNA gene. 100 ng of extracted DNA was subjected to PCR at 56° C. for strand renaturation, PCR was performed as follows: denaturation at 94° C. for 4 min, followed by 30 cycles of 94° C. for 30 s, 56° C. for 30 s, and 72° C. for 1 min.

Sequencing of amplicon gene: The library was constructed by Illumina™ TruSeq™ DNA PCR-Free Library Preparation Kit. The constructed library was subjected to Qubit quantification and library detection. After the library was qualified, microbiota sequencing was performed using the Illumina™ HiSeq™ 2500 PE250 sequencing platform.

Processing and analysis of the sequencing data: The raw data of microbiota sequencing were imported into QIIME (2019.4), and donosed with DADA2 to obtain representative amplicon variants (ASVs), which were used to construct a phylogenetic tree. After quality control, the filtered ASVs were aligned with the gene sequences in the Greengenes (V_13.5) database and performed species annotation using the Naive bayes classifier (NBC) method. In Alpha and Beta diversity analyses, a resampling depth of 10000 sequences per sample was used to ensure adequate sequences. In order to reduce the effect of species overload on the results, The results were statistically corrected by calculating the false discovery rate (FDR).

The results are shown in FIGS. 20-23 and Table 7. The results showed that at the genus level, there were significant differences in intestinal microbiota between the control group and the probiotics group. The content of *Bifidobacterium* in the control group was significantly lower than that in the probiotic group. In addition, the alpha diversity index of the probiotics group was also higher than that of the control group, but the difference was not significant in indexes (Shannon index P=0.9118 (Mann-Whitney statistic); Simpson index P=0.35268 (Mann-Whitney statistic)). In the β diversity analysis, there were differences in the overall composition of intestinal microbiota between the control group and the probiotics group, and the two groups could be significantly distinguished by the PCoA analysis results (F-value=2.4268; R-squared=0.1188; and p=0.009 (PERMANOVA)).

At the genus level, there were many different specific bacteria, whichin Coprobacillus increased significantly after using probiotics (F<0.001).

TABLE 7

| | Control group | Probiotics group | Pvalues | FDR |
|---|---|---|---|---|
| | Analysis of differences in intestinal microbiota between the two groups at the genus level | | | |
| D_5_Coprobacillus | 38.183 | 55075 | 2.17E−07 | 1.93E−05 |
| D_5_Ruminiclostridium | 9582.9 | 467.42 | 2.69E−06 | 0.00011987 |
| D_5_Butyricicoccus | 4825.7 | 1522.6 | 9.28E−06 | 0.00018877 |
| D_5_Ruminococcaceae_UCG_003 | 9141.7 | 2175.5 | 9.41E−06 | 0.00018877 |
| D_5_Clostridium_innocuum_group | 296.9 | 79573 | 1.06E−05 | 0.00018877 |
| D_5_Erysipelatoclostridium | 1063.5 | 33313 | 3.11E−05 | 0.00046104 |
| D_5_Alistipes | 280680 | 64967 | 3.89E−05 | 0.00049419 |
| D_5_Parasutterella | 24852 | 58661 | 0.00016202 | 0.001442 |
| D_5_Ruminococcus_1 | 51491 | 19309 | 0.00025718 | 0.0017088 |
| D_5_Dorea | 1648.8 | 322.35 | 0.00030703 | 0.0017088 |
| D_5_Odoribacter | 3703.3 | 917.7 | 0.00037746 | 0.0018663 |
| D_5_Rikenella | 106830 | 18411 | 0.00054891 | 0.0020444 |
| D_5_Helicobacter | 41385 | 16121 | 0.00057426 | 0.0020444 |
| D_5_Roseburia | 44371 | 27314 | 0.0010615 | 0.0033072 |
| D_5_Faecalibacterium | 766540 | 300440 | 0.0012887 | 0.0036999 |
| D_5_Prevotella_9 | 434970 | 22910 | 0.0025961 | 0.0061604 |
| D_5_Sutterella | 84556 | 31719 | 0.0026303 | 0.0061604 |
| D_5_Dialister | 12917 | 5567.9 | 0.0027349 | 0.0062412 |
| D_5_Oscillibacter | 1843.5 | 892.9 | 0.0032466 | 0.0068797 |
| D_5_Bifidobacterium | 23109 | 477820 | 0.018848 | 0.029955 |
| D_5_Desulfovibrio | 18676 | 36259 | 0.027401 | 0.041334 |
| D_5_Enterococcus | 182820 | 47499 | 0.034995 | 0.051058 |
| D_5_Escherichia_Shigella | 5240.1 | 223620 | 0.04823 | 0.068135 |
| D_5_Streptococcus | 5183.5 | 16444 | 0.049637 | 0.069026 |
| D_5_Prevotellaceae_NK3B31_group | 17987 | 3146.2 | 0.11963 | 0.15211 |
| D_5_Ruminococcaceae_UCG_014 | 50049 | 18180 | 0.13508 | 0.16932 |
| D_5_Lactobacillus | 2479500 | 884430 | 0.16394 | 0.19717 |
| D_5_Akkermansia | 91396 | 419080 | 0.28756 | 0.33238 |
| D_5_Ruminococcus_torques_group | 21859 | 24878 | 0.36456 | 0.40557 |
| D_5_Blautia | 312350 | 580010 | 0.43421 | 0.4771 |
| D_5_Staphylococcus | 26482 | 5180.9 | 0.47398 | 0.51444 |
| D_5_Prevotellaceae_UCG_001 | 96887 | 135950 | 0.53159 | 0.56323 |
| D_5_Bacteroides | 1039200 | 1192500 | 0.57971 | 0.59993 |

Example 10

This example is used to illustrate the results of an intervention with a probiotic consisting of BL-11 bacteria in 3 years and 6 months old children diagnosed with autism spectrum disorder (ASD). The probiotic was administered in the form of oral lyophilized powder at a dose of 50 billion CFU twice daily for a 90-day cycle. After administration, the children's defecation habit changed from once every 3-5 days to once every 1-2 days. Parents reported that the children's vocabulary, socialization and eye contact frequency increased, and the number of produced words increased by 3-5 words. The children have increased frequency of active feedback of their feelings, and number of unsolicited requests. The repetitive actions were reduced relative to the no-intervention condition. The parents chose to let the children continue to take probiotic, and still observe and record the continuous improvement.

Example 11

This example is used to illustrate the improvement of a probiotic consisting of BL-11 bacteria on attention deficit hyperactivity disorder (ADHD).

The patients were from Hebei Children's Hospital. The doctor diagnosed ADHD according to the Diagnostic and Statistical Manual of Mental Disorders. The patients were 6.5 years old, were hyperactive and impulsive, and also had chronic constipation and abdominal discomfort, excluded from schizophrenia, affective disorder, epilepsy, and other organic diseases.

The patient was treated with oral probiotics lyophilized powder at a dose of 60 billion CFU twice a day. The powder was taken with warm water after breakfast and dinner. The treatment lasted for 12 weeks. The Conners Parent Questionnaire was used to assess indexes, including behavior, physical, anxiety, learning, hyperactivity, etc. The results showed that impulsivity, anxiety, and hyperactivity scores decreased, defecation function improved from once every 3-4 days to once or twice every day, sometimes once every 2-3 days, defecation volume increased, and bloating and pain gradually disappeared. The children's overall mental condition improved significantly, and parents were satisfied with the results.

TABLE 8

| | Behavior | Learning | Psychosomatic | Impulse | Anxiety | Hyperactivity |
|---|---|---|---|---|---|---|
| | Results of the Conners Parent Questionnaire before and after treatment | | | | | |
| Before treatment | 1.6 | 2.1 | 0.35 | 1.34 | 0.52 | 1.38 |
| After treatment | 1.2 | 1.8 | 0.29 | 1.32 | 0.35 | 1.23 |

What is claimed is:

1. A lyophilized bacterial powder, comprising a *Bifido-bacterium animalis* subsp. *lactis* BL-11 having an accession number of CGMCC No. 20847.

2. A *Bifidobacterium animalis* subsp. *lactis* BL-11, wherein the *Bifidobacterium animalis* subsp. *lactis* BL-11 has an accession number of CGMCC No. 20847.

* * * * *